United States Patent [19]

Smith et al.

[11] 4,059,587

[45] Nov. 22, 1977

[54] CERTAIN THIAZOLIDINE COMPOUNDS

[75] Inventors: Robert L. Smith, Lansdale; Ta-Jyh Lee, Hatfield; Edward J. Cragoe, Jr., Lansdale, all of Pa.

[73] Assignee: Merck & Co., Inc., Rahway, N.J.

[21] Appl. No.: 689,311

[22] Filed: May 24, 1976

[51] Int. Cl.$^2$ ............................................ C07D 277/14
[52] U.S. Cl. .............................. 260/301; 260/268 H; 260/293.68; 260/294.8 D; 260/306.7 R; 260/345.9 R; 260/347.8; 260/599; 260/602; 260/946; 424/270; 542/400; 544/1; 560/155; 560/231

[58] Field of Search ............. 260/306.7 R, 301, 240 R, 260/268 H, 293.68, 247.1 H

*Primary Examiner*—R. J. Gallagher
*Attorney, Agent, or Firm*—Thomas E. Arther; Harry E. Westlake, Jr.; Rudolph J. Anderson, Jr.

[57] ABSTRACT

This invention relates to novel 8-aza-9-oxo-11-thia-, -11-oxothia-, and -11-dioxothia-prostanoic acid compounds, salts, and derivatives thereof and also to processes for the preparation of such compounds. These compounds have prostaglandin-like biological activity and are particularly useful as renal vasodilators, for the treatment of certain autoimmune diseases, and in preventing thrombus formation.

36 Claims, No Drawings

CERTAIN THIAZOLIDINE COMPOUNDS

SUMMARY OF THE INVENTION

This invention relates to novel 8-aza-9-oxo-11-thia,- -11-oxothia- and -11-dioxothia-prostanoic acid compounds, salts, and derivatives thereof. It also relates to compounds which are represented by the following structural formula:

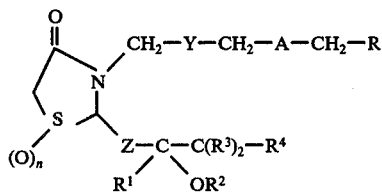

wherein R is selected from the group consisting of carboxy and a carboxy salt, said salt being formed from a pharmaceutically-acceptable cation, such as a metal cation derived from alkali metals, alkaline earth metals, and amines, such as ammonia, primary and secondary amines, and quaternary ammonium hydroxides. Especially-preferred metal cations are those derived from alkali metals, e.g., sodium, potassium, lithium, and the like, and alkaline earth metals, e.g., calcium, magnesium, and the like, and other metals, i.e., aluminum, iron, and zinc.

Pharmaceutically-acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium hydroxide, and the like.

R is also selected from alkoxycarbonyl (—COOR$^5$) wherein R$^5$ is alkyl having 1–10 carbon atoms; carbamoyl (—CONH$_2$); substituted carbamoyl (—CONR$^6$R$^7$) wherein R$^6$ and R$^7$ are selected from the group consisting of hydrogen, lower alkyl having 1–4 carbon atoms and diloweralkylaminoalkyl having 4–7 carbon atoms; and carbazoyl (—CONHNH$_2$).

A is selected from the group consisting of methylene (—CH$_2$—) and oxygen (—O—).

Y is selected from the group consisting of ethylene (—CH$_2$—CH$_2$—), cis-vinylene

or ethynylene (—C≡C—).

n = 0, 1, or 2.

Z is selected from the group consisting of ethylene or vinylene.

R$^1$ is independently selected from the group consisting of hydrogen and methyl.

R$^2$ is selected from the group consisting of hydrogen and lower alkanoyl of 1–5 carbon atoms, e.g., formyl, acetyl, propionyl, butyryl, isobutyryl, valeryl, pivaloyl, and the like.

R$^3$ is independently selected from the group consisting of hydrogen and methyl.

R$^4$ is selected from the group consisting of alkyl or branched alkyl of 3–6 carbon atoms (e.g., propyl, butyl, hexyl, isoamyl, 3,3-dimethylbutyl) or 4,4,4-trifluorobutyl.

Further:

In addition, when R$^4$ is straight chain alkyl and R$^1$ is methyl, the terminal carbon atom of R$^4$ can be joined to R$^1$ (with abstraction of hydrogen) to form a carbocyclic ring of from 6–9 carbon atoms, or when R$^4$ is straight chain alkyl and R$^1$ is hydrogen, the terminal carbon atom of R$^4$ can be joined to the carbon bearing OR$^2$ to form a carbocyclic ring of from 5–8 carbon atoms. Also, when R$^1$, R$^2$, and R$^3$ are hydrogen, R$^4$ can be a straight chain alkyl such that the terminal carbon atom of R$^4$ is joined to the hydroxy group oxygen atom (with abstraction of hydrogen) to form a cyclic ether containing 5 or 6 member atoms.

Further, R$^4$ can be OR$^{4a}$ where R$^{4a}$ is alkyl, branched alkyl of from 2–5 carbon atoms, substituted alkyl including 3,3,3-trifluoropropyl, 5- or 6-membered heterocyclic ring containing nitrogen or oxygen including pyridyl, furyl or furfuryl, or phenyl in which the phenyl ring can be substituted with one or two substituents selected from the group consisting of halogen, methyl, methoxy, or trifluoromethyl.

A preferred embodiment of this invention relates to 8-aza-9-oxo-11-thia, -11-oxothia- and -11-dioxothiaprostanoic acids having the following general formula:

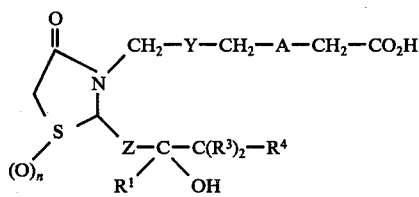

wherein A is selected from the group consisting of methylene (—CH$_2$—) and oxygen (—O—);

Y is selected from the group consisting of ethylene, cis-vinylene, or ethynylene;

n is 0, 1, or 2;

Z is ethylene or trans-vinylene;

R$^1$ and R$^3$ are as defined above; and

R$^4$ is alkyl, branched chain alkyl of 3–6 carbon atoms, 4,4,4-trifluorobutyl, or OR$^{4a}$ wherein R$^{4a}$ is as defined above.

It is to be noted that the carbon atom bearing the OR$^2$ group in formula I and the one bearing the hydroxyl group in formula II are asymmetric. This invention also covers stereoisomers in which the asymmetric center is exclusively in either one or the other of the two possible configurations, R and S.

BACKGROUND OF THE INVENTION

The compounds of formula I are described as 8-aza-9-oxo-11-thia-, -11-oxothia- and -11-dioxothia-prostanoids because of their structural relationship to the naturally-occurring prostaglandins.

The prostaglandins constitute a biologicallyprominent class of naturally-occurring, highly-functionalized C$_{20}$ fatty acids which are anabolized readily in a diverse array of mammalian tissues from three essential fatty acids; namely, 8,11,14-eicosatrienoic acid, 5,8,11,14-eicosatetraenoic acid, and 5,8,11,14,17-eicosapentaenoic acid. Each known prostaglandin is a formal derivative of the parent compound, termed "prostanoic acid;" the latter is a $C_{20}$ fatty acid covalently bridged between carbons 8 and 12 such as to form a trans, vicinally-substituted cyclopentane in which the carboxy-bearing side chain is "alpha" or below the plane of the ring, and the other side chain is "beta" or above the plane of the ring as depicted in the formula below.

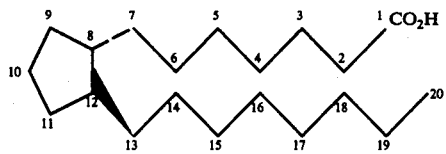

The six known primary prostaglandins, $PGE_1$, $PGE_2$, $PGE_3$, $PGF_{1\alpha}$, $PGF_{2\alpha}$, and $PGF_{3\alpha}$, resulting directly from anabolism of the above-cited essential fatty acids via the action of prostaglandin synthetase, as well as the three prostaglandins resulting from in vivo dehydration of the PGE's, i.e., $PGA_1$, $PGA_2$, and $PGA_3$, are divided into three groups; namely, the PGE, PGF, and PGA series on the basis of three distinct cyclopentane nuclear substitution patterns as illustrated below:

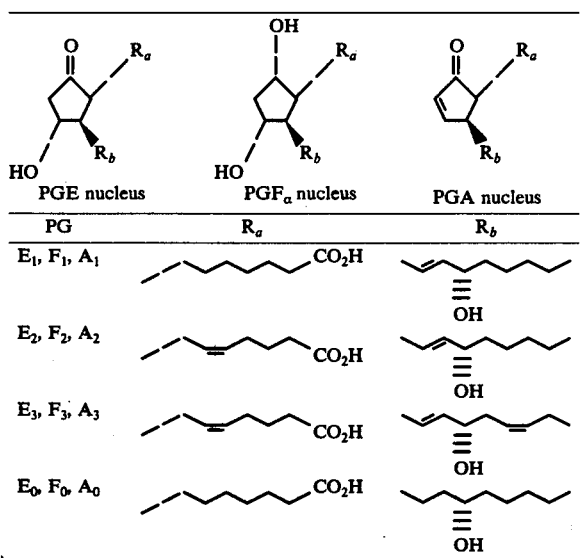

It should be noted that the arabic subscripts designate the number of carbon-carbon double bonds in the designated compound and that the Greek subscript used in the PGF series designates the stereochemistry of the C-9 hydroxyl group.

Further details concerning the prostaglandins can be found in recent reviews of their chemistry [J. E. Pike, Fortschr. Chem. Org. Naturst., 28, 313 (1970) and G. F. Bundy, A. Rep. in Med. Chem., 7, 157 (1972)]; biochemistry [J. W. Hinman, A. Rev. Biochem., 41, 161 (1972)]; pharmacology [J. R. Weeks, A. Rev. Pharm., 12, 317 (1972)]; physiological significance [E. W. Horton, Physiol. Rev., 49, 122 (1969)]; and general clinical application [J. W. Hinman, Postgrad. Med. J., 46, 562 (1970)].

The naturally-occurring prostaglandins are known to have a broad spectrum of biological activity, but at the same time are unstable metabolically. More recently, analogs of the natural prostaglandins, such as 7-[3α(3-hydroxy-3-hydrocarbylpropyl)-4-hydroxy-tetrahydro-2β-thienyl(or 2β-furyl)]heptanoic acid described in U.S. Pat. No. 3,881,017 issued Apr. 29, 1975, and U.S. Pat. No. 3,883,659 issued May 13, 1975 of Isidoros Vlattas, have been reported to have prostaglandin-like activity and also to have greater stability than the natural prostaglandins. Also, Belgian Pat. No. 828,994 discloses 4-(6-carboxyhexyl)-5-(3-hydroxy-1-trans-octenyl)-thiazoles which are said to have activity analogous to prostaglandins and to inhibit prostaglandin-destroying enzymes.

The compounds of our invention represented by formula I hereinabove were synthesized with the goal of providing therapeutic agents with unique activity which is specific in its therapeutic action but with enhanced metabolic stability, thus providing a useful medicament which is active when administered orally as well as parenterally. This goal has been accomplished by the synthesis of the compounds of the present invention which are effective therapeutic agents for the treatment of certain human and animal diseases, including the control of blood clots, for the promotion of renal vasodilation, and as regulators of the immune response.

The compounds of the present invention are useful as pharmaceutically-active compounds. Thus, these compounds are orally active in the treatment of conditions which are responsive to the actions of the natural prostaglandins. It is, of course, necessary to determine by routine laboratory testing which of the compounds of the present invention are most suitable for a specific end use and the recommended daily dosage.

In addition, the compounds of this invention appear to be broadly applicable in therapy as regulators of the immune response. The basis for their activity in this area is their ability to stimualte cyclic-AMP formation in cells. Agents, including the E prostaglandins, that increase cellular cyclic-AMP concentration interfere with the cell-mediated immune response by inhibiting lymphocyte expression in response to antigen, by inhibiting release of pathological mediators from sensitized lymphocytes, and by inhibiting the killing of target cells by such lymphocytes. Various assays which depend upon the measurement of some function of the immunologically competent lymphocyte can be used to demonstrate that the prostaglandin analogs of this invention are similarly active. For example, the release of lymphokines (proteins that are agents of inflammation and tissue destruction) from sensitized lymphocytes in culture is strongly inhibited by these analogs in low concentrations. Examples of the compounds of this invention which are particularly active in these assays include:

a. 7-[2-(3-Hydroxyoctyl)-4-oxo-3-thiazolidinyl]) heptanoic acid b. 7-[2-(3-Hydroxyoctyl)-1,1,4-trioxo-3-thiazolidinyl]-heptanoic acid Thus, it is apparent that the compounds of this invention are applicable to the treatment of those autoimmune diseases in whose pathogenesis a cell-mediated immune reaction is involved. Such diseases range from contact dermatitis to such chronic destructive diseases as rheumatoid arthritis and possibly multiple sclerosis and systemic lupus erythematosus.

The present prostaglandin analogs are also effective in preventing the rejection of transplanted organs. The biochemical basis for this action is the same as outlined in the preceeding paragraph, for the rejection of organ grafts is considered to be predominantly a cell-mediated immune phenomenon and the hallmark of organ rejection is the infiltration of cytotoxic lymphocytes into the graft. Direct evidence that the compounds of this invention can retard or prevent transplant rejection has been obtained in the rat renal allograft model; in this system, administration of the present analogs prevents the rejection of the transplanted kidney and the subsequent death of the host rat, which events invariably occur in the cases of untreated rats or those treated with the immunosuppressants.

In addition, certain of the compounds of this invention are particularly effective in inhibiting the aggregation in platelets in blood stimulated with collagen to cause platelet aggregation; and this, in inhibiting platelet aggregation, they are useful in preventing thrombus formation. An example is 7-[2-(3-Hydroxyoctyl)-4-oxo-3-thiazolidinyl]heptanoic acid.

Likewise, certain of the compounds of this invention are particularly effective in causing renal vasodilation in an in vivo assay in dogs. A particularly active compound in this assay is 7-[2-(3-Hydroxyoctyl)-4-oxo-3-thiazolidinyl]heptanoic acid.

Because of their biological activity and ready accessibility, the compounds of the invention are also useful in that they permit large scale animal testing, useful and necessary to understanding of these various disease conditions such as rejection of organ grafts, stroke (thrombus formation), impaired renal circulation, and the like. It well be appreciated that not all of the compounds of this invention have these biological activities to the same degree, but the choice of any particular ones for any given purpose will depend upon several factors including the disese state to be treated.

The compounds of this invention can be administered either topically or systemically (i.e., intravenously, subcutaneously, intramuscularly, orally, rectally, or by aerosolization in the form of sterile implants for long action).

The pharmaceutical compositions can be sterile, injectable suspensions or solutions, or solid, orallyadminsitrable, pharmaceutically-acceptable tablets or capsules; the compositions can also be intended for sublingual administration, or for suppository use.

Illustratively, a sterile injectable composition can be in the form of aqeuous or oleagenous suspensions or solutions.

The sterile, injectable composition can be an aqueous or oleagenous suspension or solution. Suspensions can be formulated according to the known art using suitable dispersing and wetting agents and suspending agents. Solutions are similarly prepared from the salt form of the compound.

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2-50 mg./ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. For either oral or parenteral use, the amount of drug to be administered is in the range of about 0.1 to 20 mg./kg. of body weight administered one to four times per day, the exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

PROCESS FOR THE SYNTHESIS OF COMPOUNDS OF THIS INVENTION

One of the preferred groups of compounds of the present invention is represented by the formula

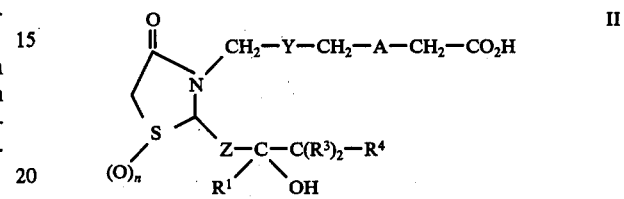

wherein A, Y, n, A, $R^1$, $R^3$, and $R^4$ are as previously stipulated. Compounds of this general type are synthesized by two principal methods.

The first method of synthesis is useful in the preparation of a preferred sub-group of compounds of the formula

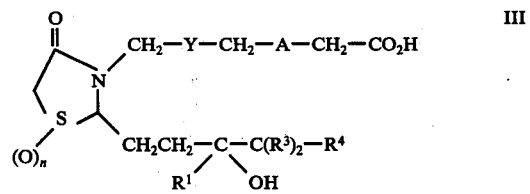

wherein A, Y, n, $R^1$, $R^3$, and $R^4$ are as previously defined. This method essentially involves condensation of an amino ester of the formula $$H_2N-CH_2-Y-CH_2-A-CH_2-CO_2R^8 \quad \text{IV}$$

wherein A and Y are as previously defined and $R^8$ is straight chain lower alkyl (ethyl or methyl) or aralkyl (benzyl) with an aldehyde of the formula

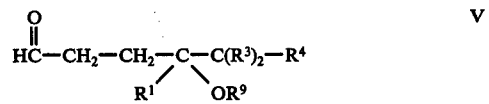

wherein $R^1$, $R^3$, and $R^4$ are as previously defined and $R^9$ is acetyl or benzyl in the presence of a suitable drying agent such as sodium or magnesium sulfate to afford key intermediate imine VI of the formula

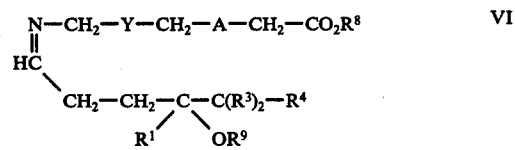

Subsequent condensation of imine VI with mercaptoacetic acid provides a derivative of compound III in which the carboxy and hydroxyl functions are either protected as esters when $R^8$ is straight chain lower alkyl and $R^9$ is acetyl or as an ester and an ether, respectively, when $R^8$ and $R^9$ are benzyl. In the first case, the diester is subjected to basic hydrolysis to produce one of the preferred sub-groups of compounds of this invention of formula III wherein $n=0$. In the second case, the ester-ether is hydrogenolyzed to afford another of the preferred sub-groups of compounds of this invention of formula III wherein $n=0$ and Y and Z are ethylene. This thia compound III is then converted by oxidation to the corresponding oxothia compound of this invention wherein $n=1$ or the dioxothia compound III wherein $n=2$. A detailed description of this method follows.

1. An aldehyde of the formula

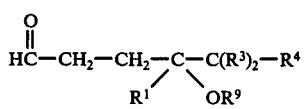    V wherein $R^1$, $R^3$, $R^4$, and $R^9$ are as previously defined is added slowly, preferably dropwise, to a freshly generated neat amino ester of the formula

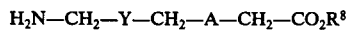    IV wherein Y, A, and $R^8$ are as previously defined maintained at a temperature of $-10°$ to $25°$ C. and, preferably, at $0°$ to $5°$ C. throughout the course of addition. Upon completing the aldehyde addition, the resulting reaction mixture is allowed to warm to room temperature, then is maintained at room temperature for 5 to 60 minutes, preferably for a period of 15 to 30 minutes, treated with an inorganic drying agent, preferably sodium or magnesium sulfate, for a period of 5 to 60 minutes at room temperature under anhydrous conditions and filtered. The collected solid is washed with a low boiling aprotic solvent, preferably chloroform, ether and the like, and the combined filtrate and washings are evaportated in vacuo at a temperature of $25°$ to $50°$ C. leaving the desired intermediate imine VI as a residual oil.

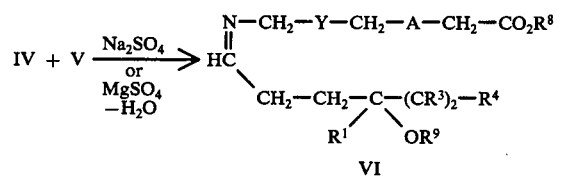

VI

2. Mercaptoacetic acid is added to a solution of immine VI in an inert solvent, preferably a higher boiling solvent such as benzene, toluene or the like, at room temperature. The resulting reaction solution is heated to and maintained at or near reflux in a Dean-Stark apparatus for a period of 2 to 24 hours to effect inital addition of the thiol compound across the imine linkage and subsequent ring closure of the intermediate amino acid with continuous removal of the liberated water providing an ester of formula VII

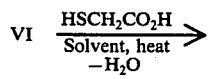

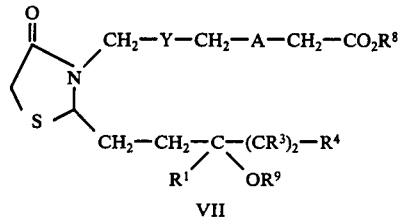

VII where $n=0$ and A, Y, $R^1$, $R^3$, $R^4$, $R^8$, and $R^9$ are as previously defined.

3. When $R^8$ is straight chain lower alkyl and $R^9$ is acyl, VII is subjected to basic hydrolysis (dilute NaOH or KOH in methanol, ethanol or tetrahydrofuran) at room temperature to remove the protecting ester functions:

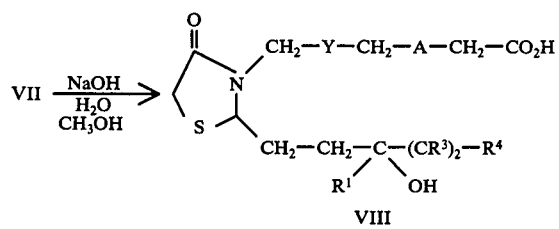

VIII

When $R^8$ and $R^9$ are aralkyl (for example, benzyl) and $R^1$ is hydrogen, VII is subjected to hydrogenolysis in an inert solvent such as ethanol, tetrahydrofuran and the like in the presence of a catalyst such as 10% Pd/C at approximately one atmosphere pressure and at room temperature for a period of time corresponding to that required for uptake of the stoichiometric quantity of hydrogen. This process provides structures of formula IX:

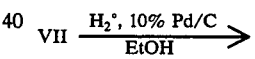

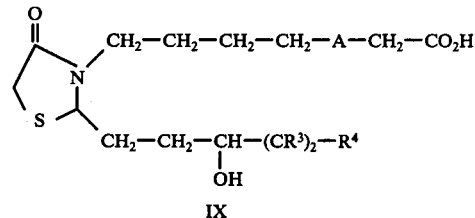

IX

4a. VII is oxidized with sodium metaperiodate in an appropriate solvent such as aqueous ethanol at a temperature of $0°$ to $5°$ C. to provide sulfoxide products of this invention ($n=1$) of formula X:

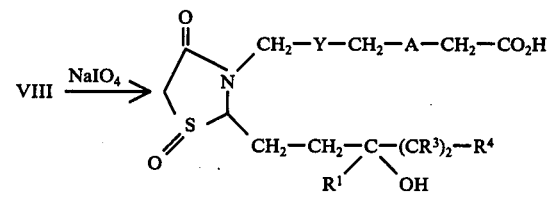

X

Likewise, oxidation of compounds IX under the same conditions as described above provides sulfoxides XI:

IX 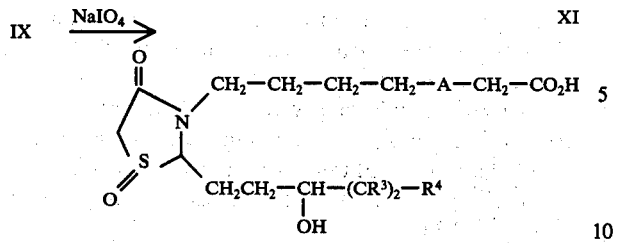 XI

4b. Either compounds VII or X can be oxidized with hydrogen peroxide (30% $H_2O_2$ in water) in a suitable solvent (ethanol, isopropanol, acetic acid and the like) in the presence of a suitable catalyst such as ammonium molybdate tetrahydrate at a temperature of from 0° to 30° C. for a period of from 24 to 72 hours to give the sulfones of this invention ($n=2$) of formula XII:

VII or X 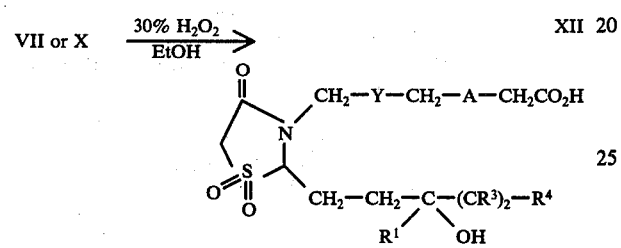 XII

Likewise, either compounds IX or XI can be oxidized under the same conditions as described above to give the sulfones of this invention ($n=2$) of formula XIII:

IX or XI 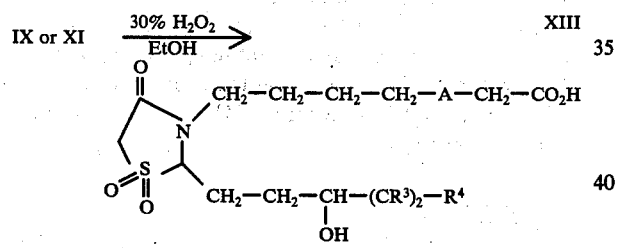 XIII

It should be noted that when Y is acetylene or cis-vinylene and $R^1$ is hydrogen, compounds VII, X, and XII can be converted to compounds IX, XI, and XIII, respectively, by catalytic hydrogenation. In addition, steps 4a and 4b may be carried out before steps (3) to provide diester or ester-ether compounds in which $n=1$ or 2 which can be subsequently O-deprotected as described above in steps (3) to afford final products X, XI, XII, and XIII.

Typical of the products which may be prepared by this method are
7-[2-(3-hydroxyoctyl)-4-oxo-3-thiazolidinyl]heptanoic acid
7-[2-(3-hydroxyoctyl)-1,4-dioxo-3-thiazolidinyl]heptanoic acid
7-[2-(3-hydroxyoctyl)-1,1,4-trioxo-3-thiazolidinyl]heptanoic acid
7-{2-[4-(4-fluorophenoxy)-3-hydroxybutyl]-1,1,4-trioxo-3-thiazolidinyl}heptanoic acid
7-{2-[2-(1-hydroxycyclohexyl)ethyl]-4-oxo-3-thiazolidinyl}-heptanoic acid The second method of synthesis of compounds of this invention is particularly useful for the preparation of another preferred sub-group of compounds of formula XIV:

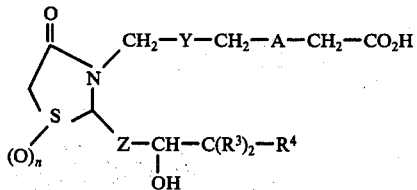 XIV wherein A, Y, and $n$ are as previously defined; Z is substituted from the group consisting of trans-vinylene

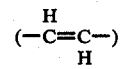

and ethylene; $R^3$ is independently selected from the group consisting of hydrogen and methyl; and $R^4$ is selected from the group consisting of alkyl or branched alkyl of 3-6 carbon atoms (e.g., propyl, butyl, hexyl, isoamyl, 3,3-dimethylbutyl) or 4,4,4-trifluorobutyl. In addition, $R^4$ can be $OR^{4a}$ where $R^{4a}$ is as previously defined.

In this method, an amino ester of formula IV:

 IV in which A and Y are as previously defined and $R^8$ is straight chain lower alkyl (methyl or ethyl) is condensed with 2,2-diethoxyacetaldehyde to provide key intermediate imine of formula XV:

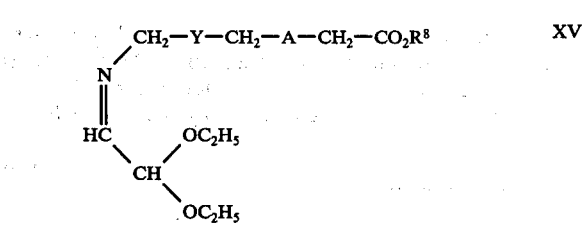 XV which is immediately condensed with mercaptoacetic acid to provide an intermediate diethyl acetal of formula XVI:

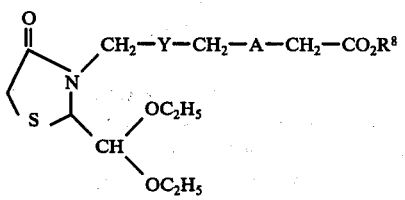 XVI which, after controlled acid hydrolysis, provides a key intermediate aldehyde of formula XVII:

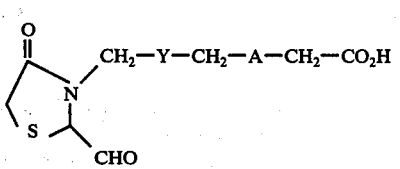 XVII

Condensation of aldehyde XVII with a phosphonate anion derived from a phosphonate of formula XVIII:

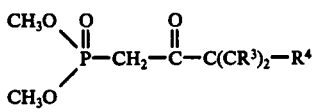

wherein $R^3$ and $R^4$ are as defined above, provides an intermediate ketone derivative of formula XIV which is subsequently reduced with alkalai borohydride reagents to provide a preferred sub-group of compounds of this invention of formula XIV in which $n=0$. The latter compounds can be converted by oxidation to the corresponding oxothia compounds of formula XIV of this invention wherein $n=1$ or the dioxothia compounds XIV wherein $n=2$. A detailed description of this method follows.

1. An amino ester of formula IV in which A, Y, and $R^8$ are as previously defined is condensed with 2,2-diethoxyacetaldehyde exactly as described in step (1) of the first method to provide intermediate imine diethyl acetal XV:

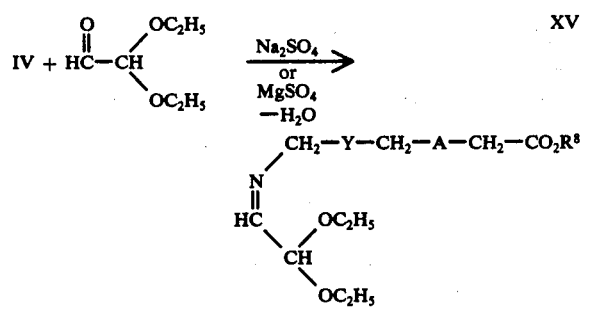

2. Imine diethyl acetal XV is then condensed with mercaptoacetic acid in an inert solvent under conditions identical to those described in step (2) of the first method to afford intermediate diethyl acetal XVI:

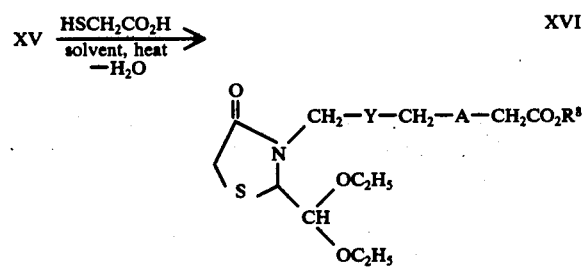

3. Diethyl acetal XVI is hydrolyzed to carboxy-aldehyde XVII in dilute aqueous acidic media such as 2N hydrochloric acid at a temperature of 40° to 100° C. for a period of 6 to 48 hours.

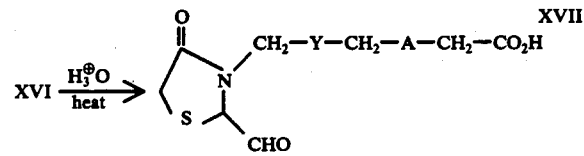

4. The sodium salt of phosphonate XVIII is generated in situ by slow addition, preferably dropwise, of one molar equivalent of XVIII over a period of 30 to 60 minutes to a stirred suspension of two equivalents of sodium hydride in an anhydrous aprotic solvent such as 1,2-dimethoxyethane, tetrahydrofuran, or hexamethylphosphoramide maintained at or below 20° C. under an inert atmosphere (e.g., nitrogen). To the resulting anion reaction mixture, maintained at or below 20° C., is added portionwise one equivalent of carboxyaldehyde XVII over a period of 1 to 2 hours. Upon completing the latter addition, the resulting reaction mixture is slowly heated to and then maintained at a temperature of 20° to 60° C. for 15 to 45 minutes providing ketone derivative XIX:

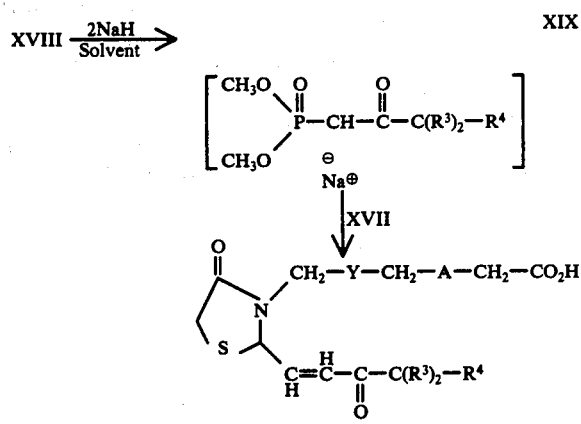

5. A cooled (0° to 5° C.) solution of ketone XIX in a suitable solvent such as methanol, ethanol, and the like, is treated with an equivalent of sodium borohydride (including 0.25 mole to convert the acid to its sodium salt) added in one addition. The resulting reaction mixture is maintained at 0° to 5° C. for 15 to 45 minutes with ice bath cooling, then at ambient temperature (up to 25° C.) for 2 to 6 hours, providing the preferred sub-group of compounds, XX, of formula XIV in which Z is trans-vinylene and $n=0$.

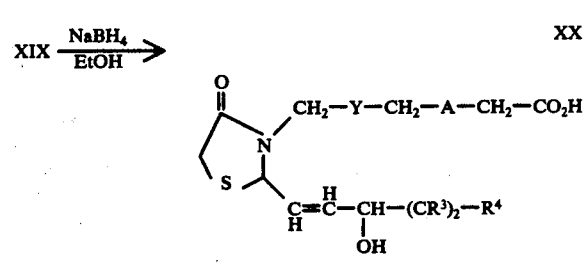

6a. XX is oxidized with sodium metaperiodate exactly as as described in step (4a) of the first method to provide sulfoxide products of this invention of formula XXI.

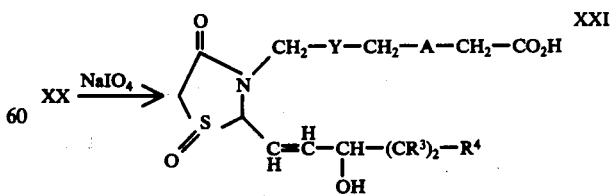

6b. Either XX or XXI can be oxidized with 30% $H_2O_2$ using conditions identical to those stipulated in step (4b) of the first method to give sulfone products of this invention of formula XXII.

XX or XXI $\xrightarrow{\text{30\% H}_2\text{O}_2}{\text{EtOH}}$ XXII

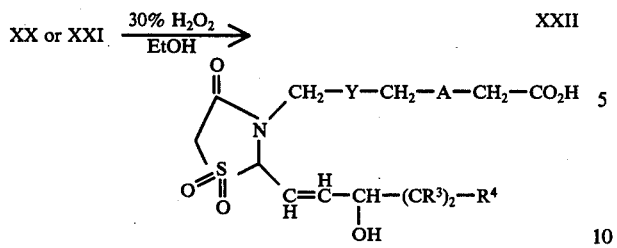

In addition, it should be noted that catalytic hydrogenation of XX, XXI, and XXII in an inert solvent at room temperature and at atmospheric pressure provides the derivatives of formula XIV of this invention wherein Y and Z are ethylene and n=0, 1, and 2, respectively.

Typical of the products which may be prepared by this method are:

7-[2-(3-hydroxy-1-trans-octenyl)-4-oxo-3-thiazolidinyl]-heptanoic acid
7-[2-(3-hydroxy-1-trans-octenyl)-1,4-dioxo-3-thiazolidinyl]-heptanoic acid
7-[2-(3-hydroxy-1-trans-octenyl)-1,1,4-trioxo-3-thiazolidinyl]heptanoic acid
7-[2-(3-hydroxyoctyl)-4oxo-3-thiazolidinyl]heptanoic acid Frequently, it is advantageous from a therapeutic standpoint to prepare compounds of this invention (formula I) in which the asymmetric carbon atom bearing $R^1$ and $OR^2$ is exclusively in the R or S configuration. One should recall that the corresponding center in the natural prostaglandins is in the S configuration; inversion of this center frequently results in a reduction of biological activity, although sometimes a marked increase in biological specificity results from this configurational change.

In our series of 8-aza-9-oxo-11-thia-, 8-aza-9-oxo-11-oxothia-, and 8-aza-9-oxo-11-dioxothiaprostanoids, compounds exclusively in the R or S configuration at this center can be produced by employing, in the first of the two fundamental methods, intermediate V which is optically active, i.e., resolved into its component R and S stereoisometric forms.

We have found it particularly advantageous to employ an optically active reagent Va:

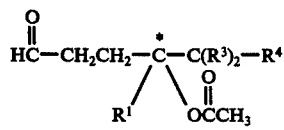

in which $R^1$, $R^3$, and $R^4$ are as previously defined, and the carbon atom marked with an asterisk (*) is exclusively in either the R or S configuration.

For example, the use of Va in method I gives intermediate imine VIa:

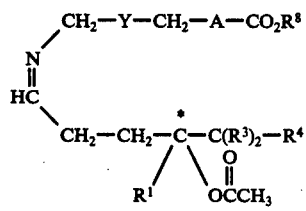

which is condensed with mercaptoacetic acid and subsequently hydrolyzed in base to yield optically active product IIIa of the invention in which n=0 and the carbon marked with an asterisk (*) is exclusively in either the R or S configuration. Subsequent oxidation of the latter product provides the corresponding optically active product IIIa wherein n=1 or 2.

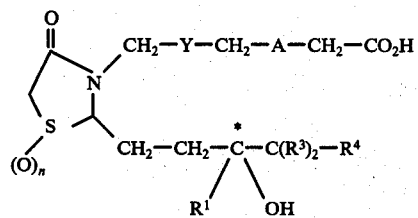

DERIVATIZATION OF PRODUCTS FROM THE MAJOR PROCESSES

The directly obtained products of Methods I and II described supra can be derivatized in a variety of ways to yield other products of formula I.

1. The fundamental process yield compounds in which R is carboxy. To obtain carboxy salts, the acid products are dissolved in a suitable solvent such as methanol, ethanol, tetrahydrofuran, and the like and the resulting solution is treated with an appropriate alkalai or alkaline earth hydroxide or alkoxide to provide the metal salt, or with an equivalent quantity of ammonia, an amine or quaternary ammomium hydroxide to yield the amine salt. In each instance, the salt either separates from the solution directly and may be collected by filtration or, when the salt is soluble, it may be recovered by evaporation of the solvent or precipitated from solution by addition of a suitable nonpolar solvent such as ether, hexane, and the like. Aqueous solutions of the carboxylic acid salts can be prepared by treating an aqueous suspension of the carboxylic acid with an equivalent amount of an alkaline earth hydroxide or oxide, alkalai metal hydroxide, carbonate or bicarbonate, ammonia, an amine or a quaternary ammonium hydroxide.

To obtain carboxy esters (i.e., compounds in which R is alkoxy carbonyl), the acid products are treated in ether with an ethereal solution of the appropriate diazoalkane. For example, methyl esters are produced by reaction of the acid products with diazomethane. To obtain products where R is carbomoyl, substituted carbamoyl, or carbazoyl, the acid product is initially converted to an active Woodward ester. For example, the acid product can be made to react with N-tert.-butyl-5-methylisoxazolium perchlorate in acetonitrile in the presence of a suitable base such as triethylamine to yield an active ester in which R is

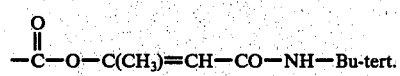

Active esters of this type can be reacted with ammonia to yield products of formula I where R is carbamoyl, with primary or secondary amines or di-lower-alkyl-aminoalkylamines to yield products in which R is substituted carbamoyl, i.e., $-CONR^6R^7$, and with hydrazine to yield products where R is carbazoyl.

2. The fundamental processes yield products in which $R^2$ is hydrogen. In compounds wherein $R^1$ is hydrogen, reaction with formic acid, acetic anhydride, propionic anhydride, butyric anhydride, isobutyric anhydride, valeric anhydride, pivalic anhydride, and the like, without solvent and at temperatures from 25° to 60 °C., provides compounds in which $R^2$ is formyl, acetyl, propionyl, butyryl, isobutyryl, valeryl, and pivaloyl, respectively.

3. Compounds of the invention in which Y, Z, or Y and Z are unsaturated groups such as vinylene or ethynylene can be hydrogenated in the presence of a suitable catalyst to other compounds of the invention in which former ethynylene groups have been reduced to vinylene or ethylene, or former vinylene groups have been reduced to ethylene. Of particular interest is the hydrogenation of a Y ethynylene group over Lindlar catalyst to give a Y cis-vinylene group.

PREPARATION OF REAGENTS

1. The reagents IV having the following general formula:

$$H_2N\text{—}CH_2\text{—}Y\text{—}CH_2\text{—}A\text{—}CH_2\text{—}CO_2R^8 \qquad \text{IV}$$

in which A, Y, and $R^8$ are as previously defined are prepared by the following process:
The potassium salt of an iodo acid I—$CH_2$—Y—$CH_2$—A—$CH_2CO_2$-K+ is made to react with potassium phthalimide in a suitable solvent such as ethanol or dimethyl formamide at a temperature of 0° to 40° C. to afford, after protonation, a N-substituted phthalimide Phth—N—$CH_2$—Y—$CH_2$—$CO_2H$ (Phth = phthaloyl) which is deblocked by treatment with hydrazine in alcohol (i.e., methanol) to yield an amino acid of the formula $H_2N$—$CH_2$—Y—$CH_2$—A—$CH_2CO_2H$ which is converted to the corresponding amino ester IV .hydrochloride by treatment in alcohol with thionyl chloride; for example, when $R^8$ is methyl, methanol is used as solvent, whereas, when $R^8$ is benzyl, benzyl alcohol is used as solvent. Neutralization of amino ester IV .hydrochloride with an equivalent quantity of a suitable base such as potassium carbonate or sodium hydroxide in water provides reagent IV. When reagents IV wherein Y is ethynylene are hydrogenated in the presence of Lindlar catalyst, reagents IV in which Y is cis vinylene are produced. Further reduction of the latter or reduction of the former in the presence of a suitable catalyst such as 5% Pd/C provides reagents IV in which Y is ethylene.

2. Reagents of the type V:

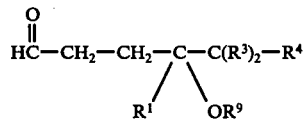

in which $R^1$, $R^3$, $R^4$, and $R^9$ are as previously defined are prepared by the following process:
3-Benzyloxy-1-propyne is made to react with ethylmagnesium bromide in an inert solvent such as tetrahydrofuran to give the Grignard adduct $C_6H_5CH_2$—O—$CH_3$—C≡CMgBr which is added to aldehydes ($R^1$ = hydrogen) or ketones ($R^1$ = methyl) of the formula $R^1$—CO—$C(R^3)_2$—$R^4$ to give the adducts $C_6H_5CH_2OCH_2C\equiv C$—$C(OMgBr)$ $R^1$)—$C(R^3)_2$—$R^4$. Treatment of the latter in situ with acetic anhydride affords the corresponding acetates $C_6H_5CH_2OCH_2C\equiv C$—$C(OCOCH_3)$ $(R^1)$—$C(R^3)_2$—$R^4$ which are hydrogenated in the presence of a suitable catalyst such as 5% Pd/C to give alcohols $HOCH_2CH_2CH_2$—$C(OCOCH_3)$ $(R^1)$—$C(R^3)_2$—$R^4$. Oxidation of the latter with Collin's reagent gives the reagents V wherein $R^9$ is acetyl.

3. The reagents Vb:

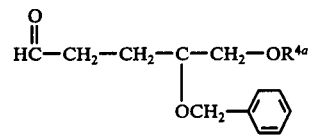

are those of type V in which $R^1$ and $R^3$ are hydrogen, $R^4$ is $OR^{4a}$ as previously defined and $R^9$ is benzyl:
Reagents Vb are prepared by converting an alcohol or phenol $R^{4a}$—OH to the corresponding sodium alkoxide or phenoxide $R^{4a}$—O$^-$Na$^+$ with sodium hydride in an aprotic solvent such as dimethylformamide followed by displacement of bromide from bromoacetaldehyde diethyl acetal to give the corresponding substituted diethyl acetals $R^{4a}$—$OCH_2CH(OEt)_2$. Acid hydrolysis of the latter in aqueous acetone provides aldehydes $R^{4a}$—$OCH_2CHO$ which are made to react with allymagnesium bromide in ether providing alcohols $R^{4a}$—$OCH_2CH(OH)CH_2CH=CH_2$. Treatment of the latter with sodium hydride in dimethylformamide provides the corresponding alkoxides which are made to react with benzyl bromide providing benzyl ethers

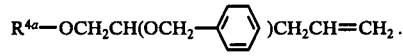

Hydroboration (reaction with diborane in tetrahydrofuran followed by $H_2O_2$ oxidation in the presence of aqueous sodium hydroxide) of the latter gives the corresponding primary alcohols

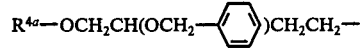

$CH_2OH$ which are converted to reagents Vb via Collin's oxidation (chromium trioxide.pyridine complex in methylene chloride).

4. The reagents Vc:

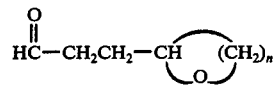

are those of type V in which $R^1$, $R_3$, and $R^9$ are hydrogen and $R^4$ is straight chain alkyl such that the terminal carbon atom of $R^4$ is joined to the hydroxyl group oxygen atom (with abstraction of hydrogen) to from a cyclic ether with 5 to 6 member atoms (n = 3 or 4). Alcohols

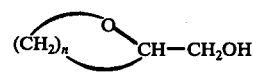

where n is as defined above are oxodized with Collins' reagent to provide aldehydes

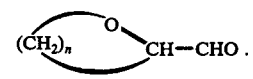

The latter are converted to reagents Vc using the directed aldol condensation procedure of G. Wittig and A. Hesse (see Organic Syntheses, Vol. 50, page 66, John Wiley and Sons, Inc., N.Y., N.Y., 1970) to generate

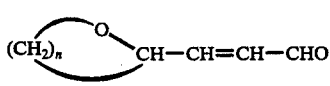

which are hydrogenated in the presence of a catalyst such as 5% Pd/C yielding Vc.

5. The optically active reagents Va:

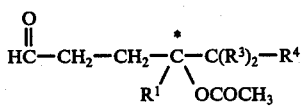

are prepared by the following process:

Aldehydes ($R^1$ = hydrogen) or ketones ($R^1$ = methyl) of the formula $R^4$—$C(R^3)_2$—CO—$R^1$ are made to react with lithium acetylide or ethynylmagnesium bromide to give the alcohols HC≡C—C($R^1$)OH—$C(R^3)_2$—$R^4$. These alcohols are resolved into their optically active R and S enantiomers by standard methods of resolution (see Organic Reactions, Vol. II, Chapter 9, page 376, John Wiley and Sons, Inc., N.Y., N.Y., 1944). After resolution, the individual enantiomers are separately and individually converted to their corresponding optically active acetates Va as follows.

The resolved alcohols HC≡C—C*($R^1$)OH—$C(R^3)_2$—$R^4$ are acetylated, preferably with acetic anyhydride, to provide acetates HC≡C—C*($R^1$) (OCOCH$_3$)—$C(R^3)_2$—$R^4$. These acetates are treated with formaldehyde and diethylamine .hydrochloride to give tertiary amines $(C_2H_5)_2$N—CH$_2$—CH$_2$—C≡C—C*($R^1$)(OCOCH$_3$)—$C(R^3)_2$-$R^4$. The latter amines are allowed to react with cyanogen bromide in ether to yield bromides Br—CH$_2$—C≡C—C*($R^1$) (OCOCH$_3$)—$C(R^3)_2$—$R^4$ which are treated with sodium benzyloxide in a suitable solvent such as dimethylformamide providing ethers $C_6H_5$  CH$_2$—O—CH$_2$—C≡C—C*($R^1$) (OCOCH$_3$)—$C(R^3)_2$-$R^4$. These ethers are hydrogenated in the presence of a suitable catalyst such as 5% Pd/C to afford primary alcohols HO—CH$_2$—CH$_2$—CH$_2$—C*($R^1$)—(OCOCH$_3$)—$C(R^3)_2$—$R^4$. The latter are oxidized with Collin's reagent to yield optically active reagents Va.

6. The reagents XVIII:

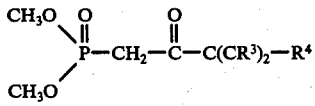

wherein $R^3$ and $R^4$ are as previously defined are prepared as follows:

Dimethyl methylphosphonate is converted to the corresponding lithium salt (CH$_3$O)—P(O)—CH$_2$—Li+ using n-butyl lithium in an aprotic solvent such as tetrahydrofuran and the like. The latter salt is made to react with methyl esters CH$_3$O$_2$—$C(CR^3)_2$—$R^4$ to provide the anion of reagents XVIII (CH$_3$O)$_2$—P(O)—C—H(Li+)—CO—$C(CR^3)_2$—$R^4$ which can be used as such in Step (4) of synthetic method II. Alternatively, the anions generated as described above may be carefully neutralized with an appropriate acid to provide reagents XVIII which can be sotred indefinitely prior to their subsequent use in the above stipulated Step (4) as described therein.

EXAMPLE 1

Preparation of 7-[2-(3-Hydroxyoctyl)-4-oxo-3-thiazolidinyl]-heptanoic Acid

Step A. Preparation of Methyl 7-[2-(3-acetyloxyoctyl)-4-oxo-3-thiazolidinyl]heptanoate 4-Acetyloxyonanal (1.03 g., 5.2 millimole) is added dropwise at 0° C. to freshly-generated methyl 7-aminoheptanoate (0.8 g., 5.1 millimole), providing an oily reaction mixture which is allowed to warm to 25° C. The reaction mixture is stirred at 25° C. for ⅓ hour, treated with anhydrous sodium sulfate (0.5 g., 3.5 millimole), stirred at 25° C. for ⅓ hours, and filtered. Collected solid is washed with chloroform (3 × 2 ml.). The combined filtrate and washings are evaporated in vacuo leaving the desired intermediate imine as a pale yellow oil.

A solution of the pale yellow oil in benzene (30 ml.) is treated with mercaptoacetic acid (0.46 g., 5.0 millimole). The resulting reaction mixture is heated at reflux for 15 hours in a Dean-Stark apparatus to remove water as generated. After removing the solvent in vacuo, the residual oily product is applied to a silica gel column (50 g.) with chloroform. Elution with chloroform (150 ml.) provides impure material; continued elution with the same eluant (150 ml.) affords the title compound as a pale yellow oil (0.86 g., 41%); pmr (CDCl$_3$) δ0.91 (3H, t), 2.03 (3H, s), 2.33 (2H, t), 2.40-3.27 (H, m), 3.33—4.00 (6H, m, containing singlets at 3.52 and 3.55) and 4.60—5.20 )2H, m).

Anal. Calcd. for $C_{21}H_{37}NO_5S$: C, 60.69; H, 8.97; N, 3.37. Found: C, 60.32; H, 9.19; N, 3.15.

Step B. Preparation of 7-[2-(3-Hydroxyoctyl)-4-oxo-3-thiazolidinyl]heptanoic Acid A turbid mixture of methyl 7-[2-(3-acetyloxyoctyl)-4-oxo-3-thiazolidinyl]heptanoate (785 mg., 1.89 milimole), 2.5 N aqueous sodium hydroxide (2ml.), and methanol (6 ml.) is stirred at 25° C. for 15 hours. After removing the solvents in vacuo below 50° C., the residual mass is acidified with 2 N hydrochloric acid and extracted twice with ether. The combined organic extract is washed with water, dried over magnesium sulfate, and filtered. In vacuo evaporation of the filtrate provides an oily residue which is applied to a silica gel column (20 g.) with chloroform. Elution with chloroform-acetic acid (50:1; v:v; 200 ml.) affords impure product; continued elution with the same eluant (600 ml.) provides the title compound as a pale yellow oil (494 mg., 73%); pmr (CDCl$_3$) δ 0.90 (3H, t), 2.34 (2H, t), 2.60—3.30 (H,m), 3.30—4.00 (4H, m, containing a singlet at 3.54), 4.53—4.93 (H, m) and 7.10 (2H, broad s, D$_2$O exchangeable). Anal. Calcd. for $C_{18}H_{33}NO_4S$: C, 60.13; H, 9.25; N, 3.90. Found: C, 59.87; H, 9.11; N, 3.55.

EXAMPLE 2

Preparation of 7-[2-(3-Hydroxyoctyl)-1,4-dioxo-3-thiazolidinyl]heptanoic Acid

Sodium metaperiodate (749 mg., 3.5 millimole) is added to a turbid solution of 7-[2-(3-hydroxyoctyl)-4-oxo-3-thiazolidinyl]heptanoic acid (1.24 g., 3.44 millimole) in methanol-water (5:4; v:v; 18 ml.) cooled in an ice bath (0° to 5° C.). After removing the cooling bath, the reaction mixture is stirred at ambient temperature for 16 hours. Precipitated solid is removed by filtration. The filtrate is diluted with cold water and extracted twice with chloroform. The combined organic extract is washed with saturated aqueous brine, dried over magnesium sulfate, and filtered. Evaporation of the filtrate in vacuo leaves an oily residue which is applied to a silica gel column (20 g.) with chloroform. Elution with chloroform-acetic acid (25:1; v:v; 310 ml.) gives an impure forerun which is discarded. Continued elution with the same eluant (330 ml.) provides the title compound as a plae yellow oil (750 mg., 58%); pmr (CDCl$_3$) δ 0.88 (3H, t), 4.47 (H, m) and 7.76 (2H, s, D$_2$O exchangeable). Anal. Calcd. for C$_{18}$H$_{33}$NO$_5$S: N, 3.73. Found: N, 3.37.

EXAMPLE 3

Preparation of
7-[2-(3-Hydroxyoctyl)-1,1,4-trioxo-3thiazolidinyl]heptanoic Acid

Step A. Preparation of Methyl 7-[2-(3-Acetyloxyoctyl)-1,1,4-trioxo-3-thiazolidinyl]heptanoate 30% Hydrogen peroxide (2.0 ml., 20 millimole) is added slowly to a stirred solution of methyl 7-[2-(3-acetyloxyoctyl)-4-oxo-3-thiazolidinyl]heptanoate (1.95 g., 4.69 millimole) and ammonium molybdate.tetrahydrate (0.1 g., catalyst) in methanol (25 ml.) maintained at 0–5°0 C. The resulting solution is allowed to warm to 25° C. and then is stirred at 25° C. for 64 hours. After diluting with water, the reaction mixture is extracted with chloroform three times. The combined organic extract is washed with water until free of peroxides, dried over magnesium sulfate, and filtered. Evaporation of the filtrate in vacuo leaves the title compound as a colorless oil (1.94 g., 92%); pmr (CDCl$_3$) δ 0.91 (3H, t), 2.08 (3H,S), 2.34 (2H, t, J=6 Hz), 2.68–3.34 (H, m), 3.35–4.28 (6H, m, containing singlets at 3.68 and 3.77), 4.28–4.70 (H, m) and 4.70–5.24 (H, m).

Step B. Preparation of 7-[2-(3-Hydroxyoctyl)-1,1,4-trioxo-3-thiazolidinyl]heptanoic Acid This compound is prepared and chromatographically purified essentially by the same procedure as described in Example 1, Step B, employing the following reagents:
Methyl 7-[2-(3-Acetyloxyoctyl)-1,1,4-trioxo-3-thiazolidinyl]-heptanoate . . . 1.94 g., 4.34 millimole
2.5 N Aqueous Sodium Hydroxide . . . 4 ml., 10 milimole
Methanol . . . 11 ml.
Silica Gel . . . 20 g.
Chloroform-Acetic Acid (25:1, v:v) . . . 400 ml.

The title compound is obtained as a pale yellow, viscous oil (0.21 g., 12%); pmr (CDCl$_3$) δ 0.90 (3H, t), 2.33 (2H, t), 2.71–3.40 (H, m), 3.40–4.28 (4H, m, containing a singlet at 3.78), 4.30–4.83 (H, m) and 7.15 (2H, broad s).

Anal. Calcd. for C$_{18}$H$_{33}$NO$_6$S: C, 55.22; H, 8,50; N, 3.58. Found: C, 55.31; H, 8.31; N, 3.21.

EXAMPLE 4

Alternate Preparation of
7-[2-(3-Hydroxyoctyl)-1,1,4-trioxo-3-thiazolidinyl]heptanoic Acid This compound is prepared and chromatographically purified essentially by the same procedure as described in Example 3, Step A, employing the following reagents:
7-[2-(3-Hydroxyoctyl)-4-oxo-3-thiazolidinyl]-heptanoic Acid . . . 1.27 g., 3.53 millimole
30% Hydrogen Peroxide . . . 1.5 ml., 15.0 millimole
Ammonium Molybdate.Tetrahydrate . . . 0.1 g., catalyst
Methanol-water (4:1; v:v) . . . 20 ml.
Silica Gel . . . 20 g.
Chloroform-Acetic Acid (25:1; v:v) . . . 500 ml.

The title compound is obtained as a pale yellow, viscous oil (510 mg., 37%) identical in all respects to the product described in Example 3, Step B.

EXAMPLE 5

Preparation of
7-{2-[4-(4-Fluorophenoxy)-3-hydroxybutyl]-1,1,4-trioxo-3-thiazolidinyl}heptanoic Acid Step A. Preparation of Benzyl 7-Aminoheptanoate Thionyl chloride (73 ml., 1.0 mole) is added dropwise over 1 hour to a stirred suspension of 7-aminoheptanoic acid (14.5 g., 0.1 mole) in benzyl alcohol (150 ml) maintained at 0°–5° C. The resulting amber solution is stirred and heated at 100° C. for 2½ hours, then allowed to stand at 25° C. for 18 hours. The reaction solution is slowly diluted with ether (1.25 l.) and stored at −30° C. for 1 ½ hours. Deposited crystals are collected, washed with ether (2 × 200 ml.) and dissolved in absolute ethanol (100 ml.) with gentle warming. The resulting solution is diluted with ether (900 ml.) and stored at 10° C. for 20 hours whereupon the benzyl 7-aminoheptanoate hydrochloride is deposited as glistening, colorless platelets (22.4 g., 83%), mp 88°–89° C. Recrystallization of a sample (0.1 g.) from ethanol-ether (1:4; v:v; 10 ml.) at −30°0 C. for 1 hour provides the analytically pure hydrochloride salt, mp 89°–90° C.; pmr (D$_2$O) δ 2.39 (2H, t), 3.13 (2H, t), 4.90 (3H, s), 5.10 (2H, s) and 7.35 (5H, s). Anal. Calcd. for C$_{14}$H$_{21}$NO$_2$.HCl: C, 61.87; H, 8.16; N, 5.15. Found: C, 61.78; H, 8,59; N, 5.00.

5 N Sodium hydroxide is added to a solution of the hydrochloride salt (2.18 g., 8,0 millimole) in water (25 ml.) at 25° C. providing a turbid mixture which is extracted immediately with chloroform (3 × ml.). The combined organic extract is dried over magnesium sulfate, filtered, and evaporated in vacuo, leaving the title compound as a pale yellow oil (1.88 g., 100%); pmr (CDCl$_3$) δ 2.39 (2H, t), 5.10 (2H, s), and 7.35 (5H, s).

Step B-1. Preparation of 4-Fluorophenoxyacetaldehyde Diethyl Acetal

A solution of 4-fluorophenol (28.1 g., 0.25 mole) in dry dimethylformamide (30 ml.) is added dropwise to a suspension of hexane (2 × 30 ml.)—prewashed sodium hydride (50% dispersion in mineral oil, 12,5 g., 0.26 mole) in dry dimethylformamide (120 ml.). After stirring at 25° C. for 10 minutes, the reaction mixture is treated with broacetaldehyde diethyl acetal (49.3 g., 9.25 mole) and heated at 100° C. for 4 hours. Upon cooling to 25° C., the reaction mixture is filtered to remove insoluble sodium bromide. The filtrate is evaporated in vacuo, leaving an oily residue which is triturated with acetone (100 ml.) at 25° C. and filtered to remove additional sodium bromide. Evaporation of the filtrate in vacuo provides a residual oil which is distilled to afford the title compound as a colorless oil (46.7 g., 82 %), bp$_{0.05}$ 87° C.; pmr (CCl$_4$) δ 1.17 (6H, t) 3.57 (2H, g), 3.61 (2H, q), 3,85 (2H, d), 4.68 (H, t) and 6.6–7.1 (4H, m).

Step B-2. Preparation of 4-Fluorophenoxyacetaldehyde

A mixture of 4-fluorophenoxyacetaldehyde diethyl acetal (30 g., 0.13 mole), acetone (150 ml.), water (150 ml.) and concentrated sulfuric acid (0.8 ml.) is stirred and heated at reflux for 16 hours. After cooling to 25°

C., the reaction mixture is extracted with methylene chloride four times. The combined organic extract is washed with aqueous sodium bicarbonate, dried over magnesium sulfate, and filtered. Evaporation of the filtrate in vacuo leaves a residual oil which is distilled to provide the title compound as a colorless oil (19 g., 94%) bp$_{0.05}$ 70° C.; pmr (CCl$_4$) δ 4.37 (2H, d), 6.6–7.1 (4H, m) and 9.68 (H, t).

Step B-3. Preparation of 5-(4-Fluorophenoxy)-1-penten-4-ol

Allyl bromide (∼0.5 g.) is added to a stirred suspension of magnesium turnings (4.49 g., 0.185 mole) in dry ether (50 ml.) at 25° C. Upon initiation of reflux, the reaction suspension is stirred and treated with a solution of allyl bromide (24.2 g., 0.2 mole) and 4-fluorophenoxyacetaldehyde (19 g., 0.123 mole) in dry ether (110 ml.) added such a rate as to maintain a gentle reflux. The resulting reaction mixture is heated at reflux for 1 hour, cooled to 0–5° C., and treated with 3.2 N sulfuric acid (70 ml.), providing a heterogeneous mixture. After separating the phases, the aqueous phase is extracted with ether three times. The organic phase is combined with the ethereal extracts and washed with 5% aqueous sodium bicarbonate, dried over magnesium sulfate, and filtered. Evaporation of the filtrate in vacuo affords an oily residue which is distilled to provide the title compound as a colorless oil (18.6 g., 77%), bp$_{0.03}$ 73° C.; pmr (CCl$_4$) δ 2.32 (2H, t), 2.54 (H, m) 3.6–4.1 (3H, m), 4.8–5.05 (H, m), 5.05–5.25 (H, m), 5.4–6.3 (H, m) and 6.67–7.1 (4H, m).

Step B-4. Preparation of 4-Benzyloxy-5-(4-fluorophenoxy) 1-pentene

A solution of 5-(4-fluorophenoxy)-1-penten-4-ol (9.81 g., 0.05 mole) in dry dimethylformamide (15 ml.) is added dropwise to a stirred suspension of hexane (2 × 10 ml.) —prewashed sodium hydride (50% dispersion in mineral oil, 2.64 g., 0.055 mole) in dry dimethylformamide (45 ml.) at 25° C. Upon cessation of gas evolution, the reaction mixture is cooled to 0°–5° C. and treated with a solution of benzyl bromide (10.3 g., 0.06 mole) in dry dimethylformamide (10 ml.). The resulting mixture is stirred at 25° C. for 16 hours, then heated at 100° C. for 1 hour. After cooling to 25° C., the reaction mixture is diluted with ice water (50 ml.) and extracted with ether four times. The combined organic extract is washed with 2 N hydrochloric acid and saturated aqueous brine, dried over magnesium sulfate and filtered. In vacuo evaporation of the filtrate leaves an oily residue which afffords the title compound upon distillation as a colorless oil (13.1 g., 92%), bp $_{0.025}$ 112°–116° C.; pmr (CCl$_4$) δ 2.37 (2H, t), 3.5–4.0 (3H, m) 4.57 (2H, s), 4.8–5.05 (H, m), 5.05–5.25 (H, m), 5.4–6.2 (H, m), 6.67–7.1 (4H, m) and 7.19 (5H, s).

Anal. Calcd. for C$_{18}$H$_{19}$FO$_2$: C, 75.50; H, 6.69. Found: C, 75.10; H, 6.70.

Step B-5. Preparation of 4-Benzyloxy-5-(4-fluorophenoxy)-pentanol

A solution of boron trifluoride.etherate (2.1 ml., 16.7 millimole) in dry tetrahydrofuran (5 ml.) is added dropwise to a stirred mixture of 4-benzyloxy-5-(4-fluorophenoxy)-1-pentene (2.86 g., 10 millimole) and sodium borohydride (0.47 g., 12.5 millimole) in dry tetrahydrofuran (25 ml.) maintained at 0°–5° C. under a nitrogen atmosphere. The resulting reaction mixture is warmed to 25° C. and maintained at 25° C. for 15 hours. After cooling to 0°–5° C., the reaction mixture is treated cautiously via successive dropwise additions of water (2 ml.), 5 N sodium hydroxide (4 ml.) and 30% hydrogen peroxide (8 ml.). After stirring at 25° C. for ½ hour, the resulting mixture is diluted with ice water and extracted with chloroform three times. The combined organic extract is washed with saturated aqueous brine, dried over magnesium sulfate, and filtered. Evaporation of the filtrate in vacuo provides the title compound as a viscous oil (3.0 g., 100%); pmr (CCl$_4$) δ 1.4–1.9 (4H, m) 3.2–4.2 (6H, m), 4.58 (2H, broad s), 6.6–7.1 (4H, m) and 7.20 (5H, s).

Step B-6. Preparation of 4-Benzyloxy-5-(4-fluorophenoxy) pentanal

Chromium trioxide (6.0 g., 0.06 mole) is added to a mechanically-stirred solution of dry pyridine (9.49 g., 0.12 mole) in methylene chloride (150 ml.) maintained at 0°–5° C. under a nitrogen atmosphere. The resulting reaction mixture is warmed to 25° C., stirred at 25° C. for ¼ hour, and treated with a solution of 4-benzyloxy-5-(4-fluorophenoxy)pentanol (3.04 g., 0.01 mole) in methylene chloride (2 ml.) which initiates precipitation of a block, intractable precipitate. After stirring at 25° C. for ¼ hour, the solution is decanted, and the insoluble precipitate washed with ether (200 ml.) The combined decantates are washed successively with 5% sodium hydroxide (3 × 100 ml.), 5% hydrochloric acid (100 ml.), and 5% aqueous sodium bicarbonate (100 ml.); dried over magnesium sulfate; and filtered. In vacuo evaporation of the filtrate affords the title compound as a pale yellow oil (2.83 g., 94%); pmr (CDCl$_3$) δ 1.80–2.20 (2H, m), 2.58 (2H, t), 3.57–4.20 (3H, m), 4.50 (H, d), 4.76 (H, d), 6.60–7.20 (4H, m) 7.30 (5H, s), and 9.75 (H, broad s).

Step C. Preparation of Benzyl 7-{2-[3-Benzyloxy-4-(4-fluoropenoxy)butyl]-4-oxo-3-thiazolidinyl}heptanoate This compound is prepared and chromatographically purified essentially by the same procedure as described in Example 1, Step A, employing the following reagents:

Benzyl 7-Aminoheptanoate . . . 1.88 g., 8.0 millimole
4-Benzyloxy-5-(4-fluorophenoxy)pentanal . . . 2.42 g., 8.0 millimole
Mercaptacetic Acid . . . 0.74 g., 8.0 millimole
Benzene . . . 50 ml.
Silica Gel . . . 120 g.
Chloroform . . . 1.36 l.

The title compound is obtained as a pale yellow, viscous oil (1.27 g., 27%); pmr (CDCl$_3$) δ 2.34 (2H, t), 2.60–3.26 (H, m), 3.30–4.12 (6H, m, containing a singlet at 3.50), 4.44–4.88 (3H, m, containing doublets at 4.54 and 4.77), 5.10 (2H, s), 6.63–7.17 (4H, m) and 7.30 (10H, s).

Anal. Calcd. for C$_{34}$H$_{40}$FNO$_5$S: C, 68.78; H, 6.79; N, 2.36. Found: C, 67.98; H, 6.88; N, 2.45.

Step D. Preparation of Benzyl 7-{2-[3-Benzyloxy-4-(4fluorophenoxy)butyl]-1,1,4-trioxo-3-thiazolidinyl} heptanoate This compound is prepared essentially by the same procedure as described in Example 2, Step A, employing the following reagents:

Benzyl 7-{2-[Benzyloxy-4-(4-fluorophenoxy)butyl]-4-oxo-3-thiazolidinyl}heptanoate . . . 1.19 g., 2.01 millimole
30% Hydrogen Peroxide . . . 1.0 ml., 10.0 millimole
Ammonium Molybdate .Tetrahydrate . . . 0.1 g., catalyst
Methanol . . . 15 ml.

The title compound is obtained as a pale yellow, viscous oil (1.1 g., 88%); pmr (CDCl$_3$) δ 2.33 (2H, t), 2.60–3.28 (H, m), 3.40–3.90 (9H, m, containing a singlet at 3.68), 5.10 (2H, s), 6.60–7.17 (4H, m) and 7.30 (10H, s).

Step E. Preparation of 7-{2-[4-(4-Fluorophenoxy)-3-hydroxybutyl]-1,1,4-trioxo-3-thiazolidinyl}heptanoic Acid A solution of benzyl 7-{2-[3-benzyloxy-4-(4-fluorophenoxy)butyl]-1,1,4-trioxo-3-thiazolidinyl}heptanoate (1.1 g., 1.76 millimole) in absolute ethanol-ethyl acetate (100:2; v:v; 102 ml.) is magnetically stirred and hydrogenated at 25° C. and atmospheric pressure in the presence of 10% palladium/charcoal until hydrogen consumption ceases (∼139 ml. of hydrogen is consumed). After removing the catalyst by filtration, the filtrate is concentrated in vacuo leaving an oily residue which is applied to a silica gel column (20 g.) with chloroform. Impurities are eluted with chloroform-acetic acid (25:1; v:v; 200 ml.); continued elution with the same eluant (375 ml.) affords the title compound as a tlc homogeneous, viscous oil (0.59 g., 75%); pmr ($CDCl_3$) δ 2.31 (2H, t), 2.73–3.37 (H, m), 3.60–4.30 (6H, m, containing singlets at 3.80 and 3.90), 4.61 (H, t), 6.67–7.60 (6H, m, containing a broad singlet at 7.30).

Anal. Calcd. for $C_{20}H_{28}FNO_7S$: C, 53.92; H, 6.33; N, 3.14. Found: C, 53.87; H, 6.10; N, 2.73.

EXAMPLE 6

Preparation of 3-Oxa-7-[2-(3-hydroxyoctyl)-4-oxo-3-thiazolidinyl]-5-heptynoic Acid Step A-1. Preparation of N-(6-Carboxy-5-oxa-2-hexynyl)phthalimide Potassium 7-iodo-3-oxa-5-heptynoate is added to a solution of potassium phthalimide (equimolar quantity) in ethanol at 25° C. The resulting solution is stirred and maintained at 25° C. until alkylation is complete. Evaporation of the reaction mixture in vacuo at 40° to 50° C. leaves a residue which is suspended in water. The aqueous suspension is acidified to Congo Red with dilute hydrochloric acid and extracted three times with ether. The combined organic extract is washed with saturated aqueous brine, dried over sodium sulfate, and filtered. In vacuo evaporation of the filutrate at 40° to 50° C. leaves the desired title compound.

Step A-2. Preparation of 7-Amino-3-oxa-5-heptanoic Acid

A solution of N-(6-carboxy-5-oxa-2-hexynyl)phthalimide and hydrazine.hydrate (2 equivalents) in methanol is stirred at 25° C. for ½ hour and then heated at reflux for 1 hour under a nitrogen atmosphere. Evaporation of the reaction mixture in vacuo at 40° C. leaves a residue which is suspended in water. Acidification (to Congo Red) of the aqueous suspension leads to precipitation of phthalhydrazide which is removed by filtration. The filtrate is carefully adjusted to the isoelectric pH by addition of dilute ammonium hydroxide whereupon the title compound precipitates from solution.

Step A-3. Preparation of Methyl 7-Amino-3-oxa-5-heptynoate.Hydrochloride

This compound is prepared essentially by the same procedure as described in Example 5, Step A, employing the following reagents and using no external heat (reaction is run at or below 25° C.):

7-Amino-3-oxa-5-heptynoic Acid . . . 2.86 g., 20 millimole
Thionyl Chloride . . . 3.57 g., 30 millimole
Anhydrous Methanol . . . 10 ml.
Ether . . . 100 ml.

The title compound is obtained as off-white crystals.

Step A-4. Preparation of Methyl 7-Amino-3-oxa-5-heptynoate

Methyl 7-amino-3-oxa-5-heptynoate.hydrochloride (1.0 g., 5.0 millimole) is dissolved in water (25 ml.) providing a clear solution which is cooled to 10° C., treated with 5 N sodium hydroxide (1.2 ml., 6.0 millimole) and immediately extracted with chloroform (3 × 25 ml.). The combined organic extract is dried over magnesium sulfate and filtered. Evaporation (in vacuo at 40° C.) of the filtrate affords the title compound as a pale yellow oil (1.6 g., 100%).

Step B. Preparation of Methyl 3-Oxa-7-[2-(3-acetyloxyoctyl)-4-oxa-3-thiazolidinyl]-5-heptynoate This compound is prepared essentially by the method described in Example 1, Step A except that the methyl 7-aminoheptanoate is replaced by methyl 7-amino-3-oxa-5-heptynoate. The title compound is obtained as a viscous oil.

Step C. Preparation of 3-Oxa-7-[2-(3-hydroxyoctyl)-4-oxo-3-thiazolidinyl]-5-heptynoic Acid This compound is prepared essentially by the method described in Example 1, Step B, except that the methyl 7-[2(3-acetyloxyoctyl)-4-oxo-3-thiazolidinyl]heptanoate is replaced by methyl 3-oxa-7-[2-(3-acetyloxyoctyl)-4-oxo-3-thiazolidinyl]-5-heptynoate. This method provides the title compound as a pale yellow viscous oil after chromatographic purification.

EXAMPLE 7

Preparation of 3-Oxa-7-[2-(3-hydroxyoctyl)-4-oxo-3-thiazolidinyl]-5-cis-heptenoic Acid A solution of 3-oxa-7-[2-(3-hydroxyoctyl)-4-oxo-3thiazolidinyl]-5-heptynoic acid in ethyl acetate is magnetically stirred and hydrogenated at room temperature and atmospheric pressure in the presence of Lindlar catalyst until one molar equivalent of hydrogen has been consumed. After removing the catalyst by filtration, the filtrate is evaporated in vacuo at 40° to 50° C. leaving the title compound as a viscous, pale yellow oil.

EXAMPLE 8

Preparation of 3-Oxa-7-[2-(3-hydroxyoctyl)-4-oxo-3-thiazolidinyl]heptanoic Acid

This compound is prepared essentially by the method as described in Example 7 except that the ethyl acetate and Lindlar catalyst are replaced by ethanol and 10% Pd/C, respectively. Hydrogenation of either 3-oxa-7-[2-(3-hydroxyoctyl)-4-oxo-3-thiazolidinyl]-5-heptynoic acid or 3-oxa-7 [2-(3-hydroxyoctyl)-4-oxo-3-thiazolidinyl]-5-cis-heptenoic acid under these conditions provides the title compound as a viscous, pale yellow oil.

EXAMPLE 9

Preparation of 3-Oxa-7-[2-(3-hydroxyoctyl)-1,4-dioxo-3-thiazolidinyl]-5-cis-heptenoic Acid This compound is prepared essentially by the method as described in Example 2 except that the 7-[2-(3-hydroxyoctyl)-4-oxo-3-thiazolidinyl]heptanoic acid is replaced by 3-oxa-7-[2-(3-hydroxyoctyl)-4-oxo-3- thiazolidinyl[-5-cis-heptenoic acid. The title compound is obtained as a pale yellow, viscous oil.

EXAMPLE 10

Preparation of 3-Oxa-7-[2-(3-hydroxyoctyl)-1,1,4-trioxo-3-thiazolidinyl]-5-cis-heptenoic Acid This compound is prepared essentially by the method as described in Example 4 except that the 7-[2-(3-hydroxyoctyl)-4-oxo-3-thiazolidinyl]heptanoic acid is replaced by 3-oxa-7-[2-(3-hydroxyoctyl)-1,4-dioxo-3-thiazolidinyl]-5-cis-heptenoic acid. This method affords the title compound as a viscous, pale yellow, oily product.

EXAMPLE 11

Preparation of 3-Oxa-7-[2-(3-hydroxyoctyl)-1,4-dioxo-3-thiazolidinyl]-heptanoic Acid This compound is prepared essentially by the method as described in Example 8 except that the 3-oxa-7-[2-(3-hydroxyoctyl)-4-oxo-3-thiazolidinyl]-5-heptynoic acid is replaced with 3-oxa-7-[2-(3-hydroxyoctyl)-1,4-dioxo-3-thiazolidinyl]-5-cis-heptenoic acid. The title compound is obtained as an essentially colorless, viscous oil.

EXAMPLE 12

Preparation of 3-Oxa-7-[2-(3-hydroxyoctyl)-1,1,4-trioxo-3-thiazolidinyl]heptanoic Acid This compound is prepared essentially by the same method as described in Example 8 except that the 3-oxa-7-[2-(3-hydroxyoctyl)-4-oxo-3-thiazolidinyl]-5-heptynoic acid is replaced with either 3-oxa-7-[2-(3-hydroxyoctyl)-1,1,4-trioxo-3-thiazolidinyl]-5-heptynoic or -5-cis-heptenoic acid. This process provides the title compound as a pale yellow, viscous oil.

EXAMPLE 13

Preparation of 7-[2-(3-Hydroxy-5-phenyl-1-trans-pentenyl)-4-oxo-3-thiazolidinyl]heptanoic Acid Step A-1. Preparation of Methyl 7-(2-Diethoxymethyl-4-oxo-3-thiazolidinyl)heptanoate This compound is prepared and chromatographed essentially by the same procedure as described in Example 1, Step A, employing the following reagents:
Methyl 7-Aminoheptanoate . . . 0.8 g., 5.1 millimole
Diethoxyacetaldehyde . . . 0.69 g., 5.2 millimole
Sodium Sulfate . . . 0.5 g., 3.5 millimole
Chloroform . . . 6 ml.
Mercaptoacetic Acid . . . 0.46 g., 5.0 millimole
Benzene . . . 30 ml.
Silica Gel . . . 50 g. Chloroform . . . 500 ml.

The title compound is obtained as an essentially colorless oil.

Step A-2. Preparation of 7-(2-Formyl-4-oxo-3-thiazolidinyl)-heptanoic Acid

A turbid solution of methyl 7-(2-diethoxymethyl-4-oxo-3-thiazolidinyl)heptanoate in 2 N hydrochloric acidacetone (2:1) is stirred and heated at reflux for 6 to 48 hours (reaction progress is monitored by t.l.c. analysis; the reaction is terminated upon reaching completion as indicated by the presence of a single polar tlc spot). The reaction mixture is cooled to room temperature, diluted with water, and extracted with ether. The organic extract is dried over sodium sulfate and filtered. In vacuo evaporation of the filtrate at 40° to 50° C. affords the title compound as a viscous oil suitable for use in Step C.

Step B. Preparation of Dimethyl 2-Oxo-4-phenyl-butylphosphonate

A solution of dimethyl methylphosphonate (12.4 g., 0.1 mole) in dry tetrahydrofuran (75 ml.) is stirred, maintained under a nitrogen atmosphere, cooled to −50° C., and treated with a 2 N solution of n-butyl lithium in hexane (50 ml., 0.1 mole) added dropwise. Upon completing the addition, the reaction mixture is kept at −50° C. for ½ hour to ensure anion formation and then is treated with ethyl 3-phenylpropionate (8.9 g., 0.05 mole) added dropwise at −50° C. After stirring for an additional 1½ hours at −50° to −40° C., the reaction mixture is poured into ice water (250 ml.) providing a turbid solution which is acidified with 2 N hydrochloric acid and extracted with ethyl acetate (4 × 75 ml.). The combined organic extract is dried over sodium sulfate and filtered. Evaporation of the filtrate in vacuo at 40° to 50° C. leaves an oily residue which is distilled to provide the title compound as an oil (11.0 g., 86%), b.p. 148°-150° C./0.1 mm.

Step C. Preparation of 7-[2-(3-Oxo-5-phenyl-1-trans-pentenyl)-4-oxo-3-thiazolidinyl]heptanoic Acid Dimethyl 2-oxo-4-phenylbutylphosphonate (1 molar equivalent) is added dropwise over a ½ hour period to a stirred suspension of sodium hydride (2 equivalents) in 1,2-dimethoxyethane maintained at or below 20° C. To the resulting reaction mixture is slowly added 7-(2-formyl)-4-oxo-3-thiazolidinyl)heptanoic acid (1 molar equivalent) with good stirring and cooling (sufficient to maintain a reaction temperature at or below 20° C.). Upon completing this addition, the reaction is stirred at ambient temperature for 1 hour, then heated at reflux for ½ hour, cooled to room temperature, and diluted with water. The aqueous mixture is acidified with dilute hydrochloric acid and extracted with ether. The organic extract is dried over sodium sulfate, filtered, and evaporated in vacuo at 40° C. leaving the title compound as an oily residue which is purified chromatographically on silica gel.

Step D. Preparation of 7-[2-(3-Hydroxy-5-phenyl-1-transpentenyl)-4-oxo-3-thiazolidinyl]heptanoic Acid Sodium borohydride (1.25 molar equivalents) is added in small portions over ½ hour to a stirred solution of 7-[2-(3-oxo-5-phenyl-1-trans-pentenyl)-4-oxo-3-thiazolidinyl]heptanoic acid (1 molar equivalent) in ethanol maintained at 0° to 5° C. Upon completing the hydride addition, the reaction mixture is stirred at 0° to 5° for ½ hour, then at ambient temperature for 2½ hours. The resulting reaction mixture is cooled to 0° to 5° C., diluted with ice water and cautiously acidified to Congo Red with 2 N hydrochloric acid providing a turbid aqueous mixture which is extracted several times with ether. The combined organic extract is dried over sodium sulfate and filtered. In vacuo evaporation of the filtrate at 40° to 50° C. leaves an oily residue which is purified by chromatography on silica gel providing the title compound as a viscous, pale yellow oil.

EXAMPLE 14

Preparation of 7-[2-(3-Hydroxy-1-trans-octenyl)-4-oxo-3-thiazolidinyl]heptanoic Acid Step A. Preparation of 7-[2-(3-Oxo-1-trans-octenyl)-4-oxo-3-thiazolidinyl]heptanoic Acid This compound is prepared essentially by the method as described in Example 13, Step C, except that the dimethyl 2-oxo-4-phenylbutylphosphonate is replaced by dimethyl 2-oxoheptylphosphonate. The title compound is obtained by this method as a viscous oil.

Step B. Preparation of 7-[2-(3-Hydroxy-1-trans-octenyl)-4-oxo-3-thiazolidinyl]heptanoic Acid This compound is prepared essentially by the method as described in Example 13, Step D, except that the 7-[2-(3-oxo-5-phenyl-1-trans-pentenyl)-4-oxo-3-thiazolidinyl]-heptanoic acid is replaced with 7-[2-(3-oxo-1-trans-octenyl)-4-oxo-3-thiazolidinyl]heptanoic acid. Chromatographic purification of the product resulting this method on silica gel affords the title compound as a pale yellow, viscous oil.

EXAMPLE 15

Preparation of 7-[2-(3-Hydroxy-1-trans-octenyl)-1,4-dioxo-3-thiazolidinyl]heptanoic Acid This compound is prepared essentially by the method as described in Example 2 except that the 7-[2-(3-hydroxyoctyl)-4-oxo-3-thiazolidinyl]heptanoic acid is replaced by 7-[2-(3-hydroxy-1-trans-octenyl)-4-oxo-3-thiazolidinyl]-heptanoic acid. This method affords the title compound as a viscous, essentially colorless oil after purification by column chromatography on silica gel.

EXAMPLE 16

Preparation of 7-{2-[2-(Tetrahydro-2H-pyran-2-yl)ethyl)-4-oxo-3-thiazolidinyl}heptanoic Acid Step A-1. Preparation of (Tetrahydro-2H-pyran-2-yl)carboxaldehyde This compound is prepared essentially by the method as described in Example 5, Step B-6, except that the 4-benzyloxy-5-(4-fluorophenoxy)pentanol is replaced by (tetrahydro-2H-pyran-2-yl)methanol. This method provides the title compound as a distillable oil.

Step A-2. Preparation of 3-(Tetrahydro-2H-pyran-2-yl)-acrolein

A solution of (tetrahydro-2H-pyran-2-yl)carboxaldehyde (1 molar equivalent) in ether is added to a cold (−70° C.), rapidly-stirred solution of the freshly-generated lithium salt of ethylidenecyclohexylamine (1 molar equivalent) in ether. The resulting reaction mixture is allowed to warm to room temperature, then is maintained at room temperature for 24 hours. After cooling to 0° to 5° C., the reaction mixture is diluted with water, stirred at 0° to 5° C. for ½ hour and evaporated in vacuo at 40° to 50° C. leaving a residual oil which is treated with oxalic acid (2molar equivalents) and water. Steam distillation of this mixture is continued until a clear distillate is obtained. The steam distillate is extracted with ether and the organic extract, dried over sodium sulfate, and filtered. Evaporation of the filtrate in vacuo at 40° C. provides the title compound as a mobile oil.

Step A-3. Preparation of 3-(Tetrahydro-2H-pyran-2-yl)propanal

This compound is prepared essentially by the method as described in Example 8 except that the 3-oxa-7-[2-(3-hydroxyoctyl)-4-oxo-3-thiazolidinyl]-5-heptynoic acid is replaced by 3-(tetrahydro-2H-pyran-2-yl)acrolein. The title compound is obtained as an essentially colorless oil.

Step B. Preparation of Methyl 7-{2-[2-(Tetrahydro-2H-pyran-2-yl)ethyl]-4-oxo-3-thiazolidinyl}heptanoate This compound is prepared essentially by the method as described in Example 1, Step A, except that the 4-acetyloxynonanal is replaced by 3-(tetrahydro-2H-pyran-2-yl)propanal. This method affords the title compound as a viscous oil.

Step C. Preparation of 7-{2-[2-(Tetrahydro-2H-pyran-2-yl)-ethyl]-4-oxo-3-thiazolidinyl}heptanoic Acid This compound is prepared essentially by the method as described in Example 1, Step B, except that the methyl 7-[2-(3-acetyloxyoctyl)-4-oxo-3-thiazolidinyl]-heptanoate is replaced by methyl 7-{2-[2-(tetrahydro-2H-pyran-2-yl)ethyl]-4-oxo-3-thiazolidinyl}heptanoate. After chromatographic purification on silica gel, the title compound is obtained as a viscous, pale yellow oil.

EXAMPLE 17

Preparation of 7-{2-[2-(1-Hydroxycyclohexyl)ethyl]-4-oxo-3-thiazolidinyl{heptanoic Acid Step A-1. Preparation of 1-(1-Acetyloxycyclohexyl)-3-benzyloxy-1-propyne A solution of 3-benzyloxy-1-propyne (1 molar equivalent) in dry ether is added dropwise to a stirred solution of ethylmagnesium bromide (1 molar equivalent) in ether at ambient temperature under a nitrogen atmosphere. Under completing the addition, the reaction mixture is stirred at ambient temperature until gas evolution (ethane generation) ceases, then is cooled to 0° to 5° C. and treated with cyclohexanone (1 molar equivalent) added dropwise at such a rate as to prevent the reaction mixture from attaining room temperature. After completing the addition, the reaction mixture is allowed to warm to room temperature, then is heated at reflux for 1 hour. In vacuo evaporation of the reaction mixture at 40° C. provides a gelatinous residue which is treated with anhydrous tetrahydrofuran and acetic anhydride (1 molar equivalent) and then heated at reflux under a nitrogen atmosphere for ½ hour. After cooling to 0° to 5° C., the reaction mixture is slowly diluted with cold 2 N hydrochloric acid, stirred at 0° to 5° C. for 15 minutes and allowed to warm to room temperature. The resulting turbid reaction mixture is extracted several times with ether. The combined organic extract is washed with water (until washings are neutral to Litmus paper) and saturated aqueous brine, dried over sodium sulfate, and filtered. Evaporation (in vacuo at 40° C.) of the filtrate provides the title compound as an essentially colorless oil.

Step A-2. Preparation of 3-(1-Acetyloxycyclohexyl)-1-propanol

This compound is prepared essentially by the method as described in Example 4, Step E, except that the benzyl 7-{2-(3-benzyloxy-4-[4-fluorophenoxy]butyl)-1,1,4-trioxo-3-thiazolidinyl}heptanoate is replaced by 1-(1-Acetyloxycyclohexyl)-3-benzyloxy-1-propyne and no chromatographic purification is needed. The title compound is obtained as an essentially colorless, mobile liquid which is used immediately in Step A-3 below.

Step A-3. Preparation of 3-(1-Acetyloxycyclohexyl)propanal

This compound is prepared essentially by the method as described in Example 5, Step B-6, except that the 4-benzyloxy-5-(4-fluorophenoxy)pentanol is replaced by 3-(1-acetyloxycyclohexyl)-1-propanol. The title compound is obtained as an oil.

Step B. Preparation of Methyl 7-{2-[2-(1-Acetyloxycyclohexyl)ethyl]-4-oxo-3-thiazolidinyl}heptanoate This compound is prepared essentially by the method as described in Example 1, Step A, except that the 4-acetyloxynonanal is replaced by 3-(1-acetyloxycyclohexyl)propanal. The title compound is obtained as a t.l.c. homogeneous oil after column chromatography on silica gel.

Step C. Preparation of 7-{2-2-(1-Hydroxycyclohexyl)ethyl]-4-oxo-3-thiazolidinyl}heptanoic Acid This compound is prepared essentially by the method as described in Example 1, Step B, except that the methyl 7-[2-(3-acetyloxyoctyl)-4-oxo-3-thiazolidinyl]-heptanoate is replaced by methyl 7-{2-[2-(1-acetyloxycyclohexyl)ethyl]-4-oxo-3-thiazolidinyl}heptanoate. Chromatographic purification of the resulting product on silica gel affords the title compound as a pale yellow, viscous oil.

EXAMPLE 18

Preparation of 7-[2-(3(S)-Hydroxyoctyl)-4-oxo-3-thiazolidinyl]heptanoic Acid

Step A-1. Preparation of 3(S)-Acetyloxy-1-octyne (S)-1-octyn-3-ol (100 g., 0.794 mole) is dissolved in pyridine (79 g., 1.0 mole) and acetic anhydride (81.6 g., 0.8 mole) is added dropwise with stirring during 1 hour. The temperature rises to 45° C. The solution is heated at 55° C. for 1 hour and then is cooled and poured into ice-cold 5% hydrochloric acid (200 ml.) providing a heterogeneous mixture which is extracted with ether. The organic extract is washed with water and saturated aqueous brine, dried over sodium sulfate, and filtered. Evaporation of the filtrate in vacuo at 40° to 50° C. yields a residual oil which is distilled to give the title compound (106.4 g., 80%), b.p. 91°-92° C./15 mm.; $[\alpha]_D^{26}$ −79° (C 3.0, CHCl$_3$).

Step A-2. Preparation of 1-Diethylamino-4(S)-acetyloxy-2-nonyne

A mixture of 3(S)-acetyloxy-1-octyne (58.5 g., 0.35 mole), diethylamine (28.5 g., 0.39 mole), paraformaldehyde (13.8 g., 0.46 mole), and p-dioxane (60 ml.) is heated on the steam bath for 17 hours, then cooled to room temperature and diluted with ether (250 ml.). The resulting solution is extracted with 5% hydrochloric acid (300 ml.) providing an aqueous extract (acidic) which is made basic with 10% sodium hydroxide solution and extracted with ether. The organic extract is dried over sodium sulfate and filtered. In vacuo evaporation of the filtrate leaves a residual oil which is distilled to provide the title compound (73.1 g., 89%), b.p. 103°-109° C./0.3 mm.; $[\alpha]_D^{26}$ −80° (C. 3.3, CHCl$_3$).

Step A-3. Preparation of 1-Bromo-4(S)-acetyloxy-2-nonyne

A solution of 1-diethylamino-4(S)-acetyloxy-2-nonyne (50.6 g., 0.20 mole) and cyanogen bromide (21.2 g., 0.20 mole) in ether (250 ml.) is allowed to stand at 25° to 27° C for 18 hours. The resulting solution is washed with 5% hydrochloric acid, water, and saturated aqueous brine, dried over sodium sulfate, and filtered. After evaporating the filtrate, the residual oil is distilled to provide the title compound (34.1 g., 65%), b.p. 97°-105° C./0.2 mm.; $[\alpha]_D^{26}$ −83° (C 3.7, CHCl$_3$).

Step A-4. Preparation of 1-Benzyloxy-4(S)-acetyloxy-2-nonyne

Benzyl alcohol (1 molar equivalent) is added dropwise to a stirred suspension of sodium hydride (1 molar equivalent) in dry dimethylformamide maintained at 0° to 5° C. throughout the addition. The reaction mixture is allowed to warm to and then is maintained at room temperature for ½ hour. After cooling to 0° to 5° C., the reaction mixture is treated with 1-bromo-4(S)-acetyloxy-2-nonyne (1 molar equivalent) added dropwise over ½ hour. The resulting reaction mixture is stirred at ambient temperature for 2 hours and the diluted with water providing a turbid mixture which is extracted with ether. The organic extract is washed with water and saturated aqueous brine, dried over sodium sulfate and filtered. Evaporation (in vacuo at 40° to 50° C.) of the filtrate leaves an oily residue which is distilled to provide the pure title compound.

Step A-5. Preparation of 4(S)-Acetyloxy-1-nonanol

This compound is prepared essentially by the method as described in Example 5, Step E, except that the benzyl 7-{2-(3-benzyloxy-4-[4-fluorophenoxy]butyl)-1,1,4-trioxo-3-thiazolidinyl}heptanoate is replaced by 1-benzyloxy-4(S)-acetyloxy-2-nonyne and no chromatographic purification is needed. The title compound is obtained as a mobile oil which is used immediately in Step A-6 below.

Step A-6. Preparation of 4(S)-Acetyloxynonanal

This compound is prepared essentially by the method as described in Example 5, Step B-6, except that the 4-benzyloxy-5-(4-fluorophenoxy)pentanol is replaced by 4(S)-acetyloxy-1-nonanol. This method provides the title compound as an essentially colorless oil.

Step B. Preparation of Methyl 7-[2-(3-(S)-Acetyloxyoctyl)-4-oxo-3-thiazolidinyl]heptanoate This compound is prepared exactly by the same method as described in Example 1, Step A, except that the 4-acetyloxynonanal is replaced by 4(S)-acetyloxynonanal. Chromatographic purification of the crude product of silica gel provides the pure title compound as a pale yellow oil.

Step C. Preparation of 7-[2-(3(S)-Hydroxyoctyl)-4-oxo-3-thiazolidinyl]heptanoic Acid This compound is prepared exactly by the same method as described in Example 1, Step B, except that the methyl 7-[2-(3-acetyloxyoctyl)-4-oxo-3-thiazolidinyl]-heptanoate is replaced by methyl 7-[2-3(S)-acetyloxyoctyl)-4-oxo-3-thiazolidinyl]heptanoate. Purification of the product resulting from this method by column chromatography on silica gel affords the pure title compound as a pale yellow oil.

EXAMPLE 19

Preparation of 7-[2-(3(R)-Hydroxyoctyl)-4-oxo-3-thiazolidinyl]heptanoic Acid

By following exactly the same procedures described in Example 18 but beginning with (R)-1-octyn-3-ol instead of (S)-1-octyn-3-ol, there are obtained successively:

Step A-1, 3(R)-Acetyloxy-1-octyne, $[\alpha]_D^{26}$ +70° (C 3.1, CHCl$_3$);

Step A-2, 1-Diethylamino-4(R)-acetyloxy-2-nonyne, $[\alpha]_D^{26}$ +74° (C 3.2, CHCl$_3$);

Step A-3, 1-Bromo-4(R)-acetyloxy-2-nonyne, $[\alpha]_D^{26}$ +75° (C 3.2, CHCl$_3$);

Step A-4, 1-Benzyloxy-4(R)-acetyloxy-2-nonyne;

Step A-5, 4(R)-Acetyloxy-1-nonanol;

Step A-6, 4(R)-Acetyloxynonanal;

Step B, Methyl 7-[2-(3(R)-Acetyloxyoctyl)-4-oxo-3-thiazolidinyl]heptanoate;

Step C, 7-[2-(3(R)-Hydroxyoctyl)-4-oxo-3-thiazolidinyl]-heptanoic Acid.

EXAMPLE 20

Preparation of 7-[2-(3-Hydroxy-3-methyloctyl)-4-oxo-3-thiazolidinyl]heptanoic Acid By following exactly the same procedures described in Example 17 but beginning with 2-heptanone rather than cyclohexanone, there are obtained successively:

Step A-1, 1-Benzyloxy-4-acetyloxy-4-methyl-2-nonyne;
Step A-2, 4-Acetyloxy-4-methyl-1-nonanol;
Step A-3, 4-Acetyloxy-4-methylnonanal;
Step B, Methyl 7-[2-(3-Acetyloxy-3-methyloctyl)-4-oxo-3-thiazolidinyl]heptanoate;
Step C, 7-[2-(3-Hydroxy-3-methyloctyl)-4-oxo-3-thiazolidinyl]heptanoic Acid.

EXAMPLE 21

Preparation of 7-[2-(3-Hydroxy-4,4-dimethyloctyl)-4-oxo-3-thiazolidinyl]heptanoic Acid By following exactly the same procedure described in Example 17 but beginning with 2,2-dimethylhexanal rather than cyclohexanone, there are obtained successively:

Step A-1, 1-Benzyloxy-4-acetyloxy-5,5-dimethyl-2-nonyne;
Step A-2, 4-Acetyloxy-5,5-dimethyl-1-nonanol;
Step A-3, 4-Acetyloxy-5,5-dimethylnononal;
Step B, Methyl 7-[2-(3-Acetyloxy-4,4-dimethyloctyl)-4-oxo-3-thiazolidinyl]heptanoate;
Step C, 7-[2-(3-Hydroxy-4,4-dimethyloctyl)-4-oxo-3-thiazolidinyl]heptanoic Acid.

EXAMPLE 22

Preparation of 7-[2-(3-Hydroxy-8,8,8-trifluorooctyl)-4-oxo-3-thiazolidinyl]heptanoic Acid By following exactly the same procedures described in Example 17 but beginning with 6,6,6-trifluorohexanal instead of cyclohexanone, there are obtained successively:

Step A-1, 1-Benzyloxy-4-acetyloxy-9,9,9-trifluoro-2-nonyne;
Step A-2, 4-Acetyloxy-9,9,9-trifluoro-1-nonanol;
Step A-3, 4-Acetyloxy-9,9,9-trifluorononanal;
Step B, Methyl 7-[2-(3-Acetyloxy-8,8,8-trifluorooctyl)-4-oxo-3-thiazolidinyl]heptanoate;
Step C, 7-[2-(3-Hydroxy-8,8,8-trifluorooctyl)-4-oxo-3-thiazolidinyl]heptanoic Acid.

EXAMPLE 23

Preparation of 7-{2-[3-Hydroxy-4-(3-pyridyloxy)butyl]-1,1,4-trioxo-3-thiazolidinyl}heptanoic Acid The synthesis of this compound is carried out by the procedures of Example 5 except that in Step B-1 of Example 5 the 4-fluorophenol is replaced by an equivalent quantity of 3-hydroxypyridine. Hence, there are obtained in order:

Step B-1, 3-Pyridyloxyacetaldehyde diethyl acetal
Step B-2, 3-Pyridyloxyacetaldehyde;
Step B-3, 5-(3-Pyridyloxy)-1-penten-4-ol;
Step B-4, 4-Benzyloxy-5-(3-pyridyloxy)-1-pentene;
Step B-5, 4-Benzyloxy-5-(3-pyridyloxy)-1-pentanol;
Step B-6, 4-Benzyloxy-5-(3-pyridyloxy)pentanal;
Step C, Benzyl 7-{2-[3-Benzyloxy-4-(3-pyridyloxy)butyl]-4-oxo-3-thiazolidinyl}heptanoate;
Step D, Benzyl 7-{2-[3-Benzyloxy-4-(3-pyridyloxy)butyl]-1,1,4-trioxo-3-thiazolidinyl}heptanoate;
Step E, 7-{2-[3-Hydroxy-4-(3-pyridyloxy)butyl]-1,1,4-trioxo-3-thiazolidinyl}heptanoic Acid.

EXAMPLE 24

Preparation of 7-[2-(3-Hydroxy-4-propoxybutyl)-1,1,4-trioxo-3-thiazolidinyl]heptanoic Acid The synthesis of this compound is carried out by the procedures of Example 5 except that in Step B-1 of Example 5 the 4-fluorophenol is replaced by an equivalent quantity of 1-propanol. Thus there are obtained in succession:

Step B-1, Propoxyacetaldehyde diethyl acetal;
Step B-2, Propoxyacetaldehyde;
Step B-3, 5-Propoxy-1-penten-4-ol;
Step B-4, 4-Benzyloxy-5-propoxy-1-pentene;
Step B-5, 4-Benzyloxy-5-propoxy-1-pentanol;
Step B-6, 4-Benzyloxy-5-propoxypentanal;
Step C, Benzyl 7-[2-(3-Benzyloxy-4-propoxybutyl)-4-oxo-3-thiazolidinyl]heptanoate;
Step D, Benzyl 7-[2-(3-Benzyloxy-4-propoxybutyl)-1,1,4-trioxo-3-thiazolidinyl]heptanoate;
Step E, 7-[2-(3-Hydroxy-4-propoxybutyl)-1,1,4-trioxo-3-thiazolidinyl]heptanoic Acid.

EXAMPLE 25

Preparation of 7-[2-(3-Hydroxy-4-propoxybutyl)-4-oxo-3-thiazolidinyl]heptanoic Acid This compound is prepared essentially by the method described in Example 5, Step E, except that the benzyl 7-{2-[3-benzyloxy-4-(4-fluorophenoxy)butyl]-1,1,4-trioxo-3-thiazolidinyl}heptanoate is replaced by benzyl 7-[2-(3-benzyloxy-4-propoxybutyl)-4-oxo-3-thiazolidinyl]heptanoate. This method provides the title compound as a viscous, pale yellow oil.

EXAMPLE 26

Preparation of 7-[2-(3-Hydroxy-4-propoxybutyl)-1,4-dioxo-3-thiazolidinyl]heptanoic Acid This compound is prepared essentially by the method described in Example 2 except that the 7-[2-(3-hydroxyoctyl)-4-oxo-3-thiazolidinyl]heptanoic acid is replaced by 7-[2-(3-hydroxy-4-propoxybutyl)-4-oxo-3-thiazolidinyl]heptanoic acid. Column chromatography of the resulting product provides the title compound as a t.l.c. homogeneous oil.

EXAMPLE 27

Preparation of Methyl 7-[2-(3-Hydroxy-4-propoxybutyl)-1,4-dioxo-3-thiazolidinyl]heptanoate A solution of diazomethane (approximately 2.5 g., 0.06 mole) in ether (100 ml.) is slowly added to a solution of 7-[2-(3-hydroxy-4-propoxybutyl)-1,4-dioxo-3-thiazolidinyl]heptanoic acid (11.3 g., 0.03 mole) in ether (50 ml.) with stirring and cooling (0° to 5° C.). The resulting solution is allowed to warm to and stand up at room temperature for 4 hours. After destroying excess diazomethane with acetic acid, the reaction solution is washed with 5% sodium bicarbonate solution and water, dried over sodium sulfate, and filtered. In vacuo evaporation of the filtrate leaves the title compound as an essentially colorless, viscous oil.

EXAMPLE 28

Preparation of
7-[2-(3-Acetyloxyoctyl)-4-oxo-3-thiazolidinyl]heptanoic Acid

A mixture of 7-[2-(3-hydroxyoctyl)-4-oxo-3-thiazolidinyl]heptanoic acid (9.0 g., 0.025 mole) and acetic anhydride (6.1 g., 0.06 mole) is heated at 60° C. for 18 hours. The resulting mixture is cooled to room temperature and dissolved in ethyl acetate providing a clear solution which is extracted with an ice-cold solution of sodium hydroxide (8 g.) in water (150 ml.). The basic solution is quickly separated and acidified with concentrated hydrochloric acid. The oily acid which separates is extracted with ether. The organic extract is washed with water, dried over sodium sulfate, and filtered. Evaporation of the filtrate in vacuo at 40° to 50° C. leaves a residual oil which is purified via application to a silica gel (150 g.) column with chloroform. Elution with chloroform-methanol (99:1; v:v) provides the title compound as a colorless, viscous oil.

By replacing the acetic anhydride used in Example 28 with an equivalent quantity of propionic anhydride, butyric anhydride, isobutyric anhydride, valeric anhydride, or pivalic anhydride and conducting the reaction as described in Example 28, there is obtained:

7-[2-(3-Propionyloxyoctyl)-4-oxo-3-thiazolidinyl]-heptanoic acid,

7-[2-(3-Butyryloxyoctyl)-4-oxo-3-thiazolidinyl]heptanoic acid,

7-[2-(3-Isobutyryloxyoctyl)-4-oxo-3-thiazolidinyl]-heptanoic acid,

7-[2-(3-Valeryloxyoctyl)-4-oxo-3-thiazolidinyl]heptanoic acid, and

7-[2-(3-Pivaloyloxyoctyl)-4-oxo-3-thiazolidinyl]heptanoic acid, respectively.

EXAMPLE 29

Preparation of
N-(2-Dimethylaminoethyl)-7-[2-(3-hydroxyoctyl)-4-oxo-3-thiazolidinyl]heptanamide A solution of 7-[2-(3-hydroxyoctyl)-4-oxo-3-thiazolidinyl]heptanoic acid (3.6 g., 10 millimole), Example 1, triethylamine (1.74 ml., 12.5 millimole) and distilled water (18 ml., 1.0 mole) in acetonitrile (100 ml.) is treated with N-t-butyl-5-methylisoxazolium perchlorate (3.0 g., 12.5 millimole). The resulting solution is evaporated in vacuo (water aspirator) at 20° to 23° C. for 4 hours providing a tacky residue which is triturated with water (150 ml.) at 0° to 5° C. for 15 minutes. After decanting the aqueous phase, the oily residue is dissolved in benzene-ether (1:1; v:v; 200 ml.). The organic extract is dried over sodium sulfate, filtered and evaporated in vacuo at 35° to 40° C. providing the desired "active ester," N-t-butyl-3-{7-[2-(3-hydroxyoctyl)-4-oxo-3-thiazolidinyl]heptanoyloxy}crotonamide, as a pale yellow oil.

A solution of 2-dimethylaminoethylamine (0.88 g., 10 millimole) in acetonitrile (25 ml.) is added to a solution of the "active ester" in acetonitrile (25 ml.) providing a clear solution which is stirred at 25° C. for 17 hours.

The solvent is removed in vacuo at 40° to 50° C. leaving a residual oil which is partitioned between ether (200 ml.) and water (2 × 100 ml.). The organic extract is washed with saturated aqueous brine (2 × 100 ml.), dried over sodium sulfate, filtered and evaporated in vacuo at 40° to 50° C. providing a crude, tan oil.

The oil is partitioned between 5% hydrochloric acid (200 ml.) and ether (2 × 100 ml.). The aqueous acid phase is slowly made basic with sodium bicarbonate (16.8 g., 0.2 mole), then with 40% aqueous sodium hydroxide (10 ml.) providing a heterogeneous mixture which is extracted with ether (100 ml.) The ethereal extract is washed with water and saturated aqueous brine, dried over sodium sulfate, and filtered. In vacuo evaporation of the filtrate leaves the title compound as a pale yellow, viscous oil.

EXAMPLE 30

Capsule Formulation

7-[2-(3-Hydroxyoctyl)-4-oxo-3-thiazolidinyl]heptanoic acid . . . 50 g.
Stearic acid (U.S.P. triple pressure) . . . 125 g. Pluronic F-68 . . . 7.5 g. Corn Starch . . . 125 g.

The stearic acid and pluronic are united in a vessel and melted using a water bath at 60° to 65° C. The heating is discontinued and the 7-[2-(3-hydroxyoctyl)-4-oxo-3-thiazolidinyl]heptanoic acid is dispersed into the mixture and the corn starch is added with stirring which is continued until the mixture cools to ambient temperature. The mixture is reduced to granules by screening and placed in a number 0 hard gelatin containing 307.5 mg. of total solids and 50 mg. of 7-[2-(3-hydroxyoctyl)-4-oxo-3-thiazolidinyl]heptanoic acid per capsule.

EXAMPLE 31

Parenteral Formulation of a Multidose Solution for Intramuscular and Intravenous Use 7-[2-(3-Hydroxyoctyl)-4-oxo-3-thiazolidinyl]heptanoic acid . . . 1 g.
Tris-(hydroxymethyl)aminomethane (Reagent Grade THAM) . . . q.s. to adjust solution to pH 7.4
Sodium Chloride (U.S.P.) . . . q.s. to yield isotonic solution
Methylparaben . . . 10 mg.
Polyparaben . . . 1 mg.
Distilled water (pyrogen-free) . . . q.s. to 10 ml.

The 7-[2-(3-hydroxyoctyl)-4-oxo-3-thiazolidinyl]-heptanoic acid suspended in about 6 ml. of the water is treated with tris-(hydroxymethyl)aminomethane with stirring until the pH reaches 7.4. The methylparaben and polyparaben are added with stirring and sufficient sodium chloride is added to produce an isotonic solution. After water is added to bring the final volume to 10 ml., the solution is sterilized by membrane filtration and placed in a vial by an aseptic technique. The solution contains the THAM salt of 7-[2-(3-hydroxyoctyl)-4-oxo-3-thiazolidinyl]heptanoic acid equivalent to 100 mg./ml. of the free acid.

EXAMPLE 32

Preparation of Suppositories

7-[2-(3-Hydroxyoctyl)-4-oxo-3-thiazolidinyl]heptanoic acid . . . 200 g.
Butylated hydroxyanisole . . . 82 mg.
Butylated hydroxytoluene . . . 82 mg.
Ethylenediamine tetraacetic acid . . . 163 mg.

Glycerine, U.S.P . . . 128 g.
Sodium chloride, microfine . . . 52.5 g.
Polyethylene glycol 6000 . . . 128 g.
Polyethylene glycol 4000 . . . 1269 g.

The polyethylene glycol 4000 and polyethylene glycol 6000 are placed in a vessel surrounded by a water bath at such a temperature as required to maintain the melted contents at 60° to 65° C. To the melt is added the butylated hydroxyanisole and butylated hydroxytoluene with stirring. Then the ethylenediamine tetraacetic acid and microfine sodium chloride are added to and dispersed in the mixture. The 7-[2-(3-hydroxyoctyl)-4-oxo-3-thiazolidinyl]heptanoic acid is then added and dispersed into the mixture. Finally, the temperature is lowered to 55° to 60° C. and the glycerine is added and dispersed.

While maintaining the temperature of 55° to 60° C. and continuous mixing, the melt is dispersed into plastic suppository cavities of a conventional suppository cold-molding device. The suppositories thus prepared contain a total of 1.7778 g. of contents of which 200 mg. are 7-[2-(3-hydroxyoctyl)-4-oxo-3-thiazolidinyl]heptanoic acid.

What is claimed is:

1. The compound of the formula

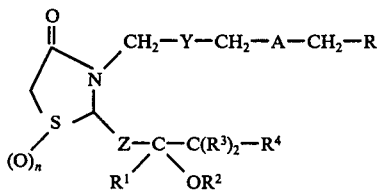

wherein
R is carboxy, a carboxy salt having the formula —COO⁻M⁺ from a metal or an amine, or derivatized carboxy in which R is selected from alkoxycarbonyl (—COOR⁵ wherein R⁵ is alkyl having 1–10 carbon atoms), carbamoyl (—CO₂NH₂), substituted carbamoyl (—CONR⁶R⁷) wherein R⁶ and R⁷ are selected from the group consisting of hydrogen, lower alkyl having 1–4 carbon atoms, and diloweralkylaminoalkyl having 4–7 carbon atoms, and carbazoyl (—CONHNH₂);
A is selected from the group consisting of methylene and oxygen;
Y is selected from the group consisting of ethylene, vinylene, and ethynylene;
n is 0, 1, or 2;
Z is selected from the group consisting of ethylene and vinylene;
R¹ is hydrogen or methyl;
R² is hydrogen or lower alkanoyl of from 1–5 carbon atoms;
R³ is hydrogen or methyl; and
R⁴ is alkyl or branched chain alkyl of from 3–6 carbon atoms, 4,4,4-trifluorobutyl, or when R⁴ is lower straight chain alkyl and R¹ is methyl, the terminal carbon atom of R⁴ can be joined to R¹ to form a polymethylene chain of from 4–7 carbon atoms, or when R⁴ is straight chain alkyl and R¹ is hydrogen, the terminal carbon atom of R⁴ can be joined to the carbon atom bearing OR² to form a polymethylene chain of from 3–6 carbon atoms.

2. The compound of claim 1 of the formula

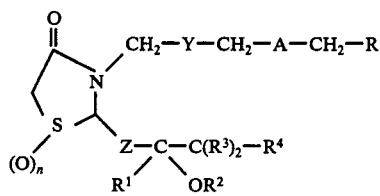

wherein
R is carboxy, a carboxy salt, or derivatized carboxy;
A is selected from the group consisting of methylene and oxygen;
Y is selected from the group consisting of ethylene, vinylene, and ethynylene;
n is 0, 1, or 2;
Z is selected from the group consisting of ethylene and vinylene;
R¹ is hydrogen or methyl;
R² is hydrogen or lower alkanoyl of from 1–5 carbon atoms;
R³ is hydrogen or methyl; and
R⁴ is alkyl or branched chain alkyl of from 3–6 carbon atoms, or 4,4,4-trifluorobutyl.

3. The compound of claim 1 wherein n is 0.

4. The compound of claim 3 wherein
A is methylene,
Y is ethylene,
Z is ethylene,
R¹, R², and R³ are hydrogen, and
R is carboxy.

5. The compond of claim 4 wherein R⁴ is butyl, which is 7-[2-(3-hydroxyoctyl)-4-oxo-3-thiazolidinyl]heptanoic acid.

6. The compound of claim 5 wherein the carbon bearing the R¹ and OR² substituents is in the "S" configuration, which is 7-[2-(3(S)-hydroxyoctyl)-4-oxo-3-thiazolidinyl]heptanoic acid.

7. The compound of claim 5 wherein the carbon bearing the R¹ and OR² substituents is in the "R" configuration, which is 7-[2-(3(R)-hydroxyoctyl)-4-oxo-3-thiazolidinyl]heptanoic acid.

8. The compound of claim 4 wherein R⁴ is 4,4,4-trifluorobutyl, which is 7-[2-(3-hydroxy-8,8,8-trifluorooctyl)-4-oxo-3-thiazolidinyl]heptanoic acid.

9. The compound of claim 1 wherein
A is methylene,
Y and Z are ethylene, and
R¹ and R³ are hydrogen.

10. The compound of claim 9 wherein R is carboxy, R² is acetyl, and R⁴ is butyl, which is 7-[2-(3-acetyloxyoctyl)-4-oxo-3-thiazolidinyl]heptanoic acid.

11. The compound of claim 9 wherein R is N-(2-dimethylaminoethyl)carbamoyl, R² is hydrogen, and R⁴ is butyl, which is N-(2-dimethylaminoethyl)-7-[2-(3-hydroxyoctyl)-4-oxo-3-thiazolidinyl]heptanamide.

12. The compound of claim 4 wherein R⁴ is butyl and the terminal carbon atom of the butyl group is joined to the carbon atom bearing the hydroxyl group with abstraction of hydrogen to form a 6-membered carbocyclic ring, which is 7-{2-[2-(1-hydroxycyclohexyl)ethyl]-4-oxo-3-thiazolidinyl}heptanoic acid.

13. The compound of claim 3 wherein A is methylene, Y and Z are ethylene, R¹ and R² are hydrogen, R³ is methyl, and R⁴ is butyl, which is 7-[2-(3-hydroxy-4,4-dimethyloctyl)-4-oxo-3-thiazolidinyl]heptanoic acid.

14. The compound of claim 3 wherein A is methylene, Y and Z are ethylene, $R^1$ is methyl, $R^2$ and $R^3$ are hydrogen, and $R^4$ is butyl, which is 7-[2-(3-hydroxy-3-methyloctyl)-4-oxo-3-thiazolidinyl]heptanoic acid.

15. The compound of claim 3 wherein
A is methylene,
Y is ethylene,
Z is trans-vinylene,
$R^1$, $R^2$, and $R^3$ are hydrogen, and
R is carboxy.

16. The compound of claim 15 wherein $R^4$ is butyl, which is 7-[2-(3-hydroxy-1-trans-octenyl)-4-oxo-3-thiazolidinyl]heptanoic acid.

17. The compound of claim 15 wherein $R^4$ is benzyl, which is 7-[2-(3-hydroxy-5-phenyl-1-trans-pentenyl)-4-oxo-3-thiazolidinyl]heptanoic acid.

18. The compound of claim 3 wherein
A is oxygen,
Z is ethylene,
$R^1$, $R^2$, and $R^3$ are hydrogen, and
$R^4$ is butyl.

19. The compound of claim 18 wherein Y is ethynylene, which is 3-oxa-7-[2-(3-hydroxyoctyl)-4-oxo-3-thiazolidinyl]-5-heptynoic acid.

20. The compound of claim 18 wherein Y is cisvinylene, which is 3-oxa-7-[2-(3-hydroxyoctyl)-4-oxo-3-thiazolidinyl]-5-cis-heptenoic acid.

21. The compound of claim 18 wherein Y is ethylene, which is 3-oxa-7-[2-(3-hydroxyoctyl)-4-oxo-3-thiazolidinyl]heptanoic acid.

22. The compound of claim 1 wherein $n$ is 1.

23. The compound of claim 22 wherein
A is methylene,
Y and Z are ethylene, and
$R^1$, $R^2$, and $R^3$ are hydrogen.

24. The compound of claim 23 wherein R is carboxy.

25. The compound of claim 24 wherein $R^4$ is butyl, which is 7-[2-(3-hydroxyoctyl)-1,4-dioxo-3-thiazolidinyl]-heptanoic acid.

26. The compound of claim 22 wherein R is carboxy, A is methylene, Y is ethylene, Z is trans-vinylene, $R^1$, $R^2$, and $R^3$ are hydrogen, and $R^4$ is butyl, which is 7-[2-(3-hydroxy-1-trans-octenyl)-1,4-dioxo-3-thiazolidinyl]-heptanoic acid.

27. The compound of claim 22 wherein
R is carboxy,
A is oxygen,
Z is ethylene,
$R^1$, $R^2$, and $R^3$ are hydrogen, and
$R^4$ is butyl.

28. The compound of claim 27 wherein y is cisvinylene, which is 3-oxa-7-[2-(3-hydroxyoctyl)-1,4-dioxo-3-thiazolidinyl]-5-cis-heptenoic acid.

29. The compound of claim 27 wherein Y is ethylene, which is 3-oxa-7-[2-(3-hydroxyoctyl)-1,4-dioxo-3-thiazolidinyl]heptanoic acid.

30. The compound of claim 1 wherein $n$ is 2.

31. The compound of claim 30 wherein
R is carboxy,
A is methylene,
Y and Z are ethylene, and
$R^1$, $R^2$, and $R^3$ are hydrogen.

32. The compound of claim 31 wherein $R^4$ is butyl, which is 7-[2-(3-hydroxyoctyl)-1,1,4-trioxo-3-thiazolidinyl]-heptanoic acid.

33. The compound of claim 30 wherein
R is carboxy,
A is oxygen,
Z is ethylene,
$R^1$, $R^2$, and $R^3$ are each hydrogen, and
$R^4$ is butyl.

34. The compound of claim 33 wherein y is cisvinylene, which is 3-oxa-7-[2-(3-hydroxyoctyl)-1,1,4-trioxo-3-thiazolidinyl]-5-cis-heptenoic acid.

35. The compound of claim 33 wherein Y is ethylene, which is 3-oxa-7-[2-(3-hydroxyoctyl)-1,1,4-trioxo-3-thiazolidinyl]heptanoic acid.

36. The compound of claim 30 wherein
R is carboxy,
A is methylene,
Y and Z are ethylene, and
$R^1$, $R^2$, and $R^3$ are hydrogen.

* * * * *

UNITED STATES PATENT AND TRADEMARK OFFICE
CERTIFICATE OF CORRECTION

PATENT NO. : 4,059,587
DATED : November 22, 1977
INVENTOR(S) : Robert L. Smith et al.

It is certified that error appears in the above-identified patent and that said Letters Patent are hereby corrected as shown below:

Column 35, Line 38, line should read,

"$COO^- M^+$ in which M is a pharmaceutically acceptable cation derived from a metal or an amine, or derivatized . . ."

Column 38, Line 11, " -heptanoic " should be " -heptenoic ".

Signed and Sealed this

Ninth Day of May 1978

[SEAL]

Attest:

RUTH C. MASON
Attesting Officer

LUTRELLE F. PARKER
Acting Commissioner of Patents and Trademarks